United States Patent
Weber et al.

(10) Patent No.: US 12,261,033 B2
(45) Date of Patent: *Mar. 25, 2025

(54) APOLIPOPROTEIN E ISOTYPE DETECTION BY MASS SPECTROMETRY

(71) Applicant: Quest Diagnostics Investments LLC, Secaucus, NJ (US)

(72) Inventors: Darren Weber, Rancho Santa Margarita, CA (US); Nigel Clarke, Vista, CA (US)

(73) Assignee: Quest Diagnostics Investments LLC, Secaucus, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/419,850

(22) Filed: Jan. 23, 2024

(65) Prior Publication Data

US 2024/0222102 A1 Jul. 4, 2024

Related U.S. Application Data

(63) Continuation of application No. 17/839,329, filed on Jun. 13, 2022, now Pat. No. 11,929,243, which is a
(Continued)

(51) Int. Cl.
*G01N 33/68* (2006.01)
*B01D 15/16* (2006.01)
(Continued)

(52) U.S. Cl.
CPC ........ *H01J 49/0045* (2013.01); *B01D 15/163* (2013.01); *B01D 15/203* (2013.01);
(Continued)

(58) Field of Classification Search
CPC H01J 49/0045; H01J 49/4215; B01D 15/163; B01D 15/203; B01D 15/424;
(Continued)

(56) References Cited

U.S. PATENT DOCUMENTS 5,772,874 A 6/1998 Quinn et al.
5,795,469 A 8/1998 Quinn et al.
(Continued)

FOREIGN PATENT DOCUMENTS

CN 1202204 A 12/1998
CN 102177436 A 9/2011
(Continued)

OTHER PUBLICATIONS

Extended European Search Report for Application No. EP18840437.0, mailed on Mar. 3, 2021, 10 pages.
(Continued)

*Primary Examiner* — Brian J. Sines
(74) *Attorney, Agent, or Firm* — Foley & Lardner LLP

(57) ABSTRACT

Provided are methods for determining the apolipoprotein E (ApoE) phenotype in a sample by mass spectrometry; wherein the ApoE allele(s) present in the sample is determined from the identity of the ions detected by mass spectrometry. In another aspect, provided herein are methods for diagnosis or prognosis of Alzheimer's disease or dementia.

13 Claims, 25 Drawing Sheets

Related U.S. Application Data continuation of application No. 16/051,171, filed on Jul. 31, 2018, now Pat. No. 11,361,953.

(60) Provisional application No. 62/539,478, filed on Jul. 31, 2017.

(51) Int. Cl.

| | | |
|---|---|---|
| *B01D 15/20* | (2006.01) | |
| *B01D 15/42* | (2006.01) | |
| *G01N 30/16* | (2006.01) | |
| *G01N 30/32* | (2006.01) | |
| *H01J 49/00* | (2006.01) | |
| *H01J 49/42* | (2006.01) | |

(52) U.S. Cl.
CPC ........... *B01D 15/424* (2013.01); *G01N 30/16* (2013.01); *G01N 30/32* (2013.01); *G01N 33/68* (2013.01); *H01J 49/4215* (2013.01); *G01N 2030/324* (2013.01)

(58) Field of Classification Search
CPC ........ G01N 30/16; G01N 30/32; G01N 33/68; G01N 2030/324
See application file for complete search history.

(56) References Cited

U.S. PATENT DOCUMENTS

| | | | |
|---|---|---|---|
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koester |
| 11,361,953 | B2 * | 6/2022 | Weber ............... G01N 30/32 |
| 11,929,243 | B2 * | 3/2024 | Weber ............... H01J 49/0045 |
| 2005/0266501 | A1 | 12/2005 | Ota et al. |
| 2009/0134323 | A1 | 5/2009 | Gross et al. |
| 2016/0195537 | A1 | 7/2016 | Sitek et al. |
| 2017/0089917 | A1 | 3/2017 | Tran et al. |

FOREIGN PATENT DOCUMENTS

| | | |
|---|---|---|
| CN | 102762986 A | 10/2012 |
| JP | 2012508886 A | 4/2012 |
| WO | 2010056815 A1 | 5/2010 |
| WO | 2017058895 A1 | 4/2017 |

OTHER PUBLICATIONS

Final Office Action mailed Nov. 9, 2020 for U.S. Appl. No. 16/051,171, filed Jul. 31, 2018.

Hirtz C., et al., "Development of New Quantitative Mass Spectrometry and Semi-Automatic Isofocusing Methods for the Determination of Apolipoprotein E Typing," Clinica Chimica Acta, Feb. 2016, vol. 454, pp. 33-38.

International Search Report and Written Opinion for Application No. PCT/US2018/044703, mailed on Nov. 16, 2018, 9 pages.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Non-Final Office Action mailed Jul. 7, 2023 for U.S. Appl. No. 17/839,329, filed Jun. 13, 2022.

Non-Final Office Action mailed Apr. 17, 2020 for U.S. Appl. No. 16/051,171, filed Jul. 31, 2018.

Non-Final Office Action mailed May 17, 2021 for U.S. Appl. No. 16/051,171, filed Jul. 31, 2018.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Rezeli M., et al., "Quantification of Total Apolipoprotein E and its Specific Isoforms in Cerebrospinal Fluid and Blood in Alzheimer's Disease and Other Neurodegenerative Diseases," EuPA Open Proteonomics, Aug. 7, 2015, vol. 8, pp. 137-143.

Robb D.B., et al., "Atmospheric Pressure Photoionization: An Ionization Method for Liquid Chromatography-Mass Spectrometry," Analytical Chemistry, 2000, vol. 72 (15), pp. 3653-3659.

Salm P., et al., "The Quantification of Sirolimus by High-Performance Liquid Chromatography-Tandem Mass Spectrometry and Microparticle Enzyme Immunoassay in Renal Transplant Recipients," Clinical Therapeutics, 2000, vol. 22 Suppl B, pp. B71-B85.

Simon R., et al., "Total ApoE And ApoE4 Isoform Assays in an Alzheimer'S Disease Case-Control Study by Targeted Mass Spectrometry (n=669): A Pilot Assay for Methionine-Containing Proteotypic Peptides," Molecular Cellular Proteomics, Nov. 2012, vol. 11 (11), pp. 1389-1403.

Taylor P.J., et al., "Simultaneous Quantification of Tacrolimus and Sirolimus in Human Blood, by High-Performance Liquid Chromatography—Tandem Mass Spectrometry," Therapeutic Drug Monitoring, 2000, vol. 22 (5), pp. 608-612.

Tubbs K.A., et al., "High-Throughput MS-Based Protein Phenotyping: Application to Haptoglobin," Proteomics, Dec. 2005, vol. 5 (18), pp. 5002-5007.

Van Den Broek I., et al., "AutomatedMultiplexLC-MS/MSAssayforQuantifyingSerumApolipoproteinsA-I,B,C-I,C-II,C-III, andEwithQualitativeApolipoproteinEPhenotyping," Clinical Chemistry, Jan. 2016, vol. 62 (1), pp. 188-197.

Wildsmith K.R., et al., "Method for the Simultaneous Quantitation of Apolipoprotein E Isoforms Using Tandem Mass Spectrometry," Analytical Biochemistry, Dec. 2009, vol. 395 (1), pp. 116-118.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatography-Tandem Mass Spectrometry," Journal of Chromatography A, 1999, vol. 854, pp. 23-35.

* cited by examiner

FIGURE 7

| Allele Frequency* | E2 | E3 | E4 |
|---|---|---|---|
| N | 40 | 512 | 86 |
| % Occurrence | 6.27% | 80.25% | 13.48% |

| | Isoform-specific amino acid difference | | Allele frequency (%) | |
|---|---|---|---|---|
| | 112 | 158 | General | AD |
| Apo-E2 | Cys | Cys | 8.4 | 3.9 |
| Apo-E3 | Cys | Arg | 77.9 | 59.4 |
| Apo-E4 | Arg | Arg | 13.7 | 36.7 |

| Phenotype Frequency | E2/E2 | E2/E3 | E2/E4 | E3/E3 | E3/E4 | E4/E4 |
|---|---|---|---|---|---|---|
| N | 1 | 30 | 7 | 210 | 63 | 8 |
| % Occurrence | 0.31% | 9.40% | 2.20% | 65.83% | 19.75% | 2.51% |

FIGURE 12

|  | AD Mark | MS Algorithm |
|---|---|---|
| AD | 79 | 80 |
| Non-AD | 80 | 79 |

| False Positive Rate |
|---|
| 3.78% |
| False Negative Rate |
| 4.40% |

APOLIPOPROTEIN E ISOTYPE DETECTION BY MASS SPECTROMETRY

CROSS-REFERENCE TO RELATED PATENT APPLICATIONS

This application is a continuation application of U.S. patent application Ser. No. 17/839,329, filed Jun. 13, 2022, which is a continuation application of U.S. patent application Ser. No. 16/051,171, filed Jul. 31, 2018, now U.S. Pat. No. 11,361,953, which claims benefit of U.S. Provisional Application No. 62/539,478, filed Jul. 31, 2017, each of which is incorporated by reference herein in its entirety.

FIELD OF THE INVENTION

The invention relates to the detection or quantitation of apolipoprotein E. In a particular aspect, the invention relates to methods for detecting apolipoprotein E or alleles thereof by mass spectrometry.

BACKGROUND OF THE INVENTION

Alzheimer's disease is the most common form of dementia affecting the elderly population. Alzheimer's disease is characterized by a progressive decay of cognitive abilities, in particular, memory and learning. Apolipoprotein E (APOE) is associated with a marked increase in developing Alzheimer's disease. The human APOE gene has three polymorphic alleles, ε2, ε3 and ε4 that result in six different phenotypes: ε2/ε2, ε2/ε3, ε3/ε3, ε2/ε4, ε3/ε4 and ε4/ε4.

The accuracy and sensitivity of current clinical diagnostic methods to predict or diagnose Alzheimer's disease is low. An accurate and sensitive assay for detecting apolipoprotein E is needed. In particular, an accurate and sensitive assay for detecting various isoforms is needed.

SUMMARY OF THE INVENTION

Provided herein are methods for detecting or determining the amount of apolipoprotein E (APOE) in a sample by mass spectrometry, including tandem mass spectrometry.

In certain embodiments, the methods provided herein are for detecting or determining the amount of apolipoprotein E comprises (a) purifying apolipoprotein E in the sample; (b) ionizing apolipoprotein E in the sample; and (c) detecting or determining the amount of the apolipoprotein E ion(s) by mass spectrometry; wherein the amount of the apolipoprotein E ion(s) is related to the amount of apolipoprotein E in the sample.

In certain embodiments, the methods provided herein are for determining the apolipoprotein E (ApoE) phenotype in a sample, said method comprising: (a) purifying ApoE in the sample; (b) ionizing ApoE in the sample to produce one or more ion(s) of ApoE; (c) detecting the ion(s) from step (b) by mass spectrometry; wherein the ApoE allele(s) present in the sample is determined from the identity of the ions detected in step (c).

In some embodiments, purifying provided herein comprises liquid chromatography. In some embodiments, the liquid chromatography comprises high performance liquid chromatography (HPLC).

In some embodiments, ApoE in the samples is digested. In some embodiments, ApoE is digested by trypsin. In some embodiments, the digested ApoE is microwaved. In some embodiments, ApoE is digested by rapid enzyme digest microwave technology.

In some embodiments, purifying provided herein comprises solid phase extraction (SPE).

In some embodiments, the ionization comprises electrospray ionization (ESI). In some embodiments, the ionization comprises ionizing in positive mode. In some embodiments, the ionization comprises ionizing in negative mode.

In some embodiments, methods provided herein further comprise adding an internal standard. In some embodiments, the internal standard is isotopically labeled.

In some embodiments, the phenotype determined by the method provided herein is ApoE2/ApoE2. In some embodiments, the phenotype is ApoE2/ApoE3. In some embodiments, the phenotype is ApoE2/ApoE4. In some embodiments, the phenotype is ApoE3/ApoE3. In some embodiments, the phenotype is ApoE3/ApoE4. In some embodiments, the phenotype is ApoE4/ApoE4.

In some embodiments, the ApoE2/ApoE2 is determined by the presence of a precursor ion(s) having a mass/charge ratio of 555.15±0.5. In some embodiments, the ApoE2/ApoE2 is determined by the presence of a precursor ion(s) having a mass/charge ratio of 612.19±0.5. In some embodiments, the ApoE2/ApoE2 is determined by the presence of a fragment ion(s) having a mass/charge ratio selected from the group consisting of 665.72±0.5 and 835.93±0.5. In some embodiments, the ApoE2/ApoE2 is determined by the presence of fragment ions having mass/charge ratios of 665.72±0.5 and 835.93±0.5. In some embodiments, the ApoE2/ApoE2 is determined by the presence of a fragment ion(s) having a mass/charge ratio selected from the group consisting of 866.99±0.5 and 982.08±0.5. In some embodiments, the ApoE2/ApoE2 is determined by the presence of fragment ions having mass/charge ratios of 866.99±0.5 and 982.08±0.5. In some embodiments, the ApoE2/ApoE2 is determined by the presence of a fragment ion(s) having a mass/charge ratio selected from the group consisting of 665.72±0.5, 835.93±0.5, 866.99±0.5 and 982.08±0.5. In some embodiments, the ApoE2/ApoE2 is determined by the presence of fragment ions having mass/charge ratios of 665.72±0.5, 835.93±0.5, 866.99±0.5 and 982.08±0.5.

In some embodiments, the ApoE2/ApoE3 is determined by the presence of a precursor ion(s) having a mass/charge ratio of 555.15±0.5. In some embodiments, the ApoE2/ApoE3 is determined by the presence of a precursor ion(s) having a mass/charge ratio of 612.19±0.5. In some embodiments, the ApoE2/ApoE3 is determined by the presence of a precursor ion(s) having a mass/charge ratio of 475.05±0.5. In some embodiments, the ApoE2/ApoE3 is determined by the presence of a fragment ion(s) having a mass/charge ratio selected from the group consisting of 665.72±0.5 and 835.93±0.5. In some embodiments, the ApoE2/ApoE3 is determined by the presence of fragment ions having mass/charge ratios of 665.72±0.5 and 835.93±0.5. In some embodiments, the ApoE2/ApoE3 is determined by the presence of a fragment ion(s) having a mass/charge ratio selected from the group consisting of 866.99±0.5 and 982.08±0.5. In some embodiments, the ApoE2/ApoE3 is determined by the presence of fragment ions having mass/charge ratios of 866.99±0.5 and 982.08±0.5. In some embodiments, the ApoE2/ApoE3 is determined by the presence of a fragment ion(s) having a mass/charge ratio selected from the group consisting of 374.42±0.5 and 502.55±0.5. In some embodiments, the ApoE2/ApoE3 is determined by the presence of fragment ions having mass/charge ratios of 374.42±0.5 and 502.55±0.5. In some embodiments, the ApoE2/ApoE3 is determined by the presence of a fragment ion(s) having a mass/charge ratio selected from the group consisting of 374.42±0.5, 502.55±0.5, 665.72±0.5, 835.93±0.5, 866.99±0.5 and 982.08±0.5. In some embodiments, the ApoE2/ApoE3 is determined by the presence of fragment ions having mass/charge ratios of 374.42±0.5, 502.55±0.5, 665.72±0.5, 835.93±0.5, 866.99±0.5 and 982.08±0.5.

In some embodiments, the ApoE2/ApoE4 is determined by the presence of a precursor ion(s) having a mass/charge ratio of 555.15±0.5. In some embodiments, the ApoE2/ApoE4 is determined by the presence of a precursor ion(s) having a mass/charge ratio of 612.19±0.5. In some embodiments, the ApoE2/ApoE4 is determined by the presence of a precursor ion(s) having a mass/charge ratio of 475.05±0.5. In some embodiments, the ApoE2/ApoE4 is determined by the presence of a precursor ion(s) having a mass/charge ratio of 503.56±0.5. In some embodiments, the ApoE2/ApoE4 is determined by the presence of a fragment ion(s) having a mass/charge ratio selected from the group consisting of 665.72±0.5 and 835.93±0.5. In some embodiments, the ApoE2/ApoE4 is determined by the presence of fragment ions having mass/charge ratios of 665.72±0.5 and 835.93±0.5. In some embodiments, the ApoE2/ApoE4 is determined by the presence of a fragment ion(s) having a mass/charge ratio selected from the group consisting of 866.99±0.5 and 982.08±0.5. In some embodiments, the ApoE2/ApoE4 is determined by the presence of fragment ions having mass/charge ratios of 866.99±0.5 and 982.08±0.5. In some embodiments, the ApoE2/ApoE4 is determined by the presence of a fragment ion(s) having a mass/charge ratio selected from the group consisting of 374.42±0.5 and 502.55±0.5. In some embodiments, the ApoE2/ApoE4 is determined by the presence of fragment ions having mass/charge ratios of 374.42±0.5 and 502.55±0.5. In some embodiments, the ApoE2/ApoE4 is determined by the presence of a fragment ion(s) having a mass/charge ratio selected from the group consisting of 649.74±0.5 and 892.96±0.5. In some embodiments, the ApoE2/ApoE4 is determined by the presence of fragment ions having mass/charge ratios of 649.74±0.5 and 892.96±0.5. In some embodiments, the ApoE2/ApoE4 is determined by the presence of a fragment ion(s) having a mass/charge ratio selected from the group consisting of 374.42±0.5, 502.55±0.5, 649.74±0.5, 665.72±0.5, 835.93±0.5, 866.99±0.5, 892.96±0.5, and 982.08±0.5. In some embodiments, the ApoE2/ApoE4 is determined by the presence of fragment ions having mass/charge ratios of 374.42±0.5, 502.55±0.5, 649.74±0.5, 665.72±0.5, 835.93±0.5, 866.99±0.5, 892.96±0.5, and 982.08±0.5.

In some embodiments, the ApoE3/ApoE3 is determined by the presence of a precursor ion(s) having a mass/charge ratio of 612.19±0.5. In some embodiments, the ApoE3/ApoE3 is determined by the presence of a precursor ion(s) having a mass/charge ratio of 475.05±0.5. In some embodiments, the ApoE3/ApoE3 is determined by the presence of a fragment ion(s) having a mass/charge ratio selected from the group consisting of 866.99±0.5 and 982.08±0.5. In some embodiments, the ApoE3/ApoE3 is determined by the presence of fragment ions having mass/charge ratios of 866.99±0.5 and 982.08±0.5. In some embodiments, the ApoE3/ApoE3 is determined by the presence of a fragment ion(s) having a mass/charge ratio selected from the group consisting of 374.42±0.5 and 502.55±0.5. In some embodiments, the ApoE3/ApoE3 is determined by the presence of fragment ions having mass/charge ratios of 374.42±0.5 and 502.55±0.5. In some embodiments, the ApoE3/ApoE3 is determined by the presence of a fragment ion(s) having a mass/charge ratio selected from the group consisting of 374.42±0.5, 502.55±0.5, 866.99±0.5 and 982.08±0.5. In some embodiments, the ApoE3/ApoE3 is determined by the presence of fragment ions having mass/charge ratios of 374.42±0.5, 502.55±0.5, 866.99±0.5 and 982.08±0.5.

In some embodiments, the ApoE3/ApoE4 is determined by the presence of a precursor ion(s) having a mass/charge ratio of 612.19±0.5. In some embodiments, the ApoE3/ApoE4 is determined by the presence of a precursor ion(s) having a mass/charge ratio of 475.05±0.5. In some embodiments, the ApoE3/ApoE4 is determined by the presence of a precursor ion(s) having a mass/charge ratio of 503.56±0.5. In some embodiments, the ApoE3/ApoE4 is determined by the presence of a fragment ion(s) having a mass/charge ratio selected from the group consisting of 866.99±0.5 and 982.08±0.5. In some embodiments, the ApoE3/ApoE4 is determined by the presence of fragment ions having mass/charge ratios of 866.99±0.5 and 982.08±0.5. In some embodiments, the ApoE3/ApoE4 is determined by the presence of a fragment ion(s) having a mass/charge ratio selected from the group consisting of 374.42±0.5 and 502.55±0.5. In some embodiments, the ApoE3/ApoE4 is determined by the presence of fragment ions having mass/charge ratios of 374.42±0.5 and 502.55±0.5. In some embodiments, the ApoE3/ApoE4 is determined by the presence of a fragment ion(s) having a mass/charge ratio selected from the group consisting of 649.74±0.5 and 892.96±0.5. In some embodiments, the ApoE3/ApoE4 is determined by the presence of fragment ions having mass/charge ratios of 649.74±0.5 and 892.96±0.5. In some embodiments, the ApoE3/ApoE4 is determined by the presence of a fragment ion(s) having a mass/charge ratio selected from the group consisting of 374.42±0.5, 502.55±0.5, 649.74±0.5, 866.99±0.5, 892.96±0.5, and 982.08±0.5. In some embodiments, the ApoE3/ApoE4 is determined by the presence of fragment ions having mass/charge ratios of 374.42±0.5, 502.55±0.5, 649.74±0.5, 866.99±0.5, 892.96±0.5, and 982.08±0.5.

In some embodiments, the ApoE3/ApoE4 is determined by the presence of a precursor ion(s) having a mass/charge ratio of 475.05±0.5. In some embodiments, the ApoE3/ApoE4 is determined by the presence of a precursor ion(s) having a mass/charge ratio of 503.56±0.5. In some embodiments, the ApoE3/ApoE4 is determined by the presence of a fragment ion(s) having a mass/charge ratio selected from the group consisting of 374.42±0.5 and 502.55±0.5. In some embodiments, the ApoE3/ApoE4 is determined by the presence of fragment ions having mass/charge ratios of 374.42±0.5 and 502.55±0.5. In some embodiments, the ApoE3/ApoE4 is determined by the presence of a fragment ion(s) having a mass/charge ratio selected from the group consisting of 649.74±0.5 and 892.96±0.5. In some embodiments, the ApoE3/ApoE4 is determined by the presence of fragment ions having mass/charge ratios of 649.74±0.5 and 892.96±0.5. In some embodiments, the ApoE3/ApoE4 is determined by the presence of a fragment ion(s) having a mass/charge ratio selected from the group consisting of 374.42±0.5, 502.55±0.5, 649.74±0.5, and 892.96±0.5. In some embodiments, the ApoE3/ApoE4 is determined by the presence of fragment ions having mass/charge ratios of 374.42±0.5, 502.55±0.5, 649.74±0.5, and 892.96±0.5.

In some embodiments, the presence of ApoE4 allele indicates increased risk of developing Alzheimer's disease. In some embodiments, the presence of ApoE4/ApoE4 alleles indicates increased risk of developing Alzheimer's disease.

In some embodiments, quantitation of total ApoE comprises measuring a precursor ion having a mass/charge ratio of 485.06±0.5. In some embodiments, quantitation of total ApoE comprises measuring a fragment ion(s) with a mass/charge ratio selected from 489.51±0.5 and 588.64±0.5.

In certain embodiments, the limit of quantitation of the methods is less than or equal to 10 ng/mL. In some embodiments, the limit of quantitation of the methods is less than or equal to 5 ng/mL. In some embodiments, the limit of quantitation of the methods is less than or equal to 4 ng/mL. In some embodiments, the limit of quantitation of the methods is less than or equal to 3 ng/mL. In some embodiments, the limit of quantitation of the methods is less than or equal to 2 ng/mL. In some embodiments, the limit of quantitation of the methods is less than or equal to 1 ng/mL. In some embodiments, the limit of quantitation of the methods is less than or equal to 0.5 ng/mL. In some embodiments, the limit of quantitation of the methods is less than or equal to 0.2 ng/ml. In some embodiments, the limit of quantitation of the methods is less than or equal to 0.1 ng/mL.

In some embodiments, the limit of detection of the methods is less than or equal to 5 ng/mL. In some embodiments, the limit of detection of the methods is less than or equal to 1 ng/mL. In some embodiments, the limit of detection of the methods is less than or equal to 0.5 ng/mL. In some embodiments, the limit of detection of the methods is less than or equal to 0.1 ng/mL. In some embodiments, the limit of detection of the methods is less than or equal to 0.05 ng/mL. In some embodiments, the limit of detection of the methods is less than or equal to 0.01 ng/mL.

In some embodiments, ApoE is not derivatized prior to mass spectrometry.

In some embodiments, ApoE is derivatized prior to mass spectrometry.

In certain embodiments, the sample is a body fluid. In some embodiments, the sample is cerebrospinal fluid (CSF). In some embodiments, the sample is plasma or serum. In some embodiments, the sample is whole blood. In some embodiments, the sample is saliva or urine.

In some embodiments, the methods may include adding an agent to the sample in an amount sufficient to deproteinate the sample.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Samples are purified herein by various means to allow removal of one or more interfering substances, e.g., one or more substances that would interfere with the detection of selected ApoE parent and daughter ions by mass spectrometry.

As used herein, the term "test sample" refers to any sample that may contain ApoE. As used herein, the term "body fluid" means any fluid that can be isolated from the body of an individual. For example, "body fluid" may include blood, plasma, serum, bile, saliva, urine, tears, perspiration, and the like.

As used herein, the term "derivatizing" means reacting two molecules to form a new molecule. Derivatizing agents may include isothiocyanate groups, dinitro-fluorophenyl groups, nitrophenoxycarbonyl groups, and/or phthaldehyde groups, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr. A* 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 μm. As used in this context, the term "about" means ±10%. In a preferred embodiment the column contains particles of about 60 μm in diameter.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means ±10%. In a preferred embodiment the analytical column contains particles of about 4 μm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6, 124, 137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification", "limit of quantitation" or "LOQ" refers to the point where measurements become quantitatively meaningful. The analyte response at this LOQ is identifiable, discrete and reproducible with a precision of 20% and an accuracy of 80% to 120%.

As used herein, the term "limit of detection" or "LOD" is the point at which the measured value is larger than the uncertainty associated with it. The LOD is defined arbitrarily as 2 standard deviations (SD) from the zero concentration.

As used herein, an "amount" of ApoE in a body fluid sample refers generally to an absolute value reflecting the mass of ApoE detectable in volume of body fluid. However, an amount also contemplates a relative amount in comparison to another ApoE amount. For example, an amount of ApoE in a body fluid can be an amount which is greater than or less than a control or normal level of ApoE normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 7 shows ApoE allele frequency based on 319 individual serum samples determined by LC-MS/MS.

FIG. 12 shows logistic regression model vs. ADMark.

DETAILED DESCRIPTION OF THE INVENTION

Figure 1A:
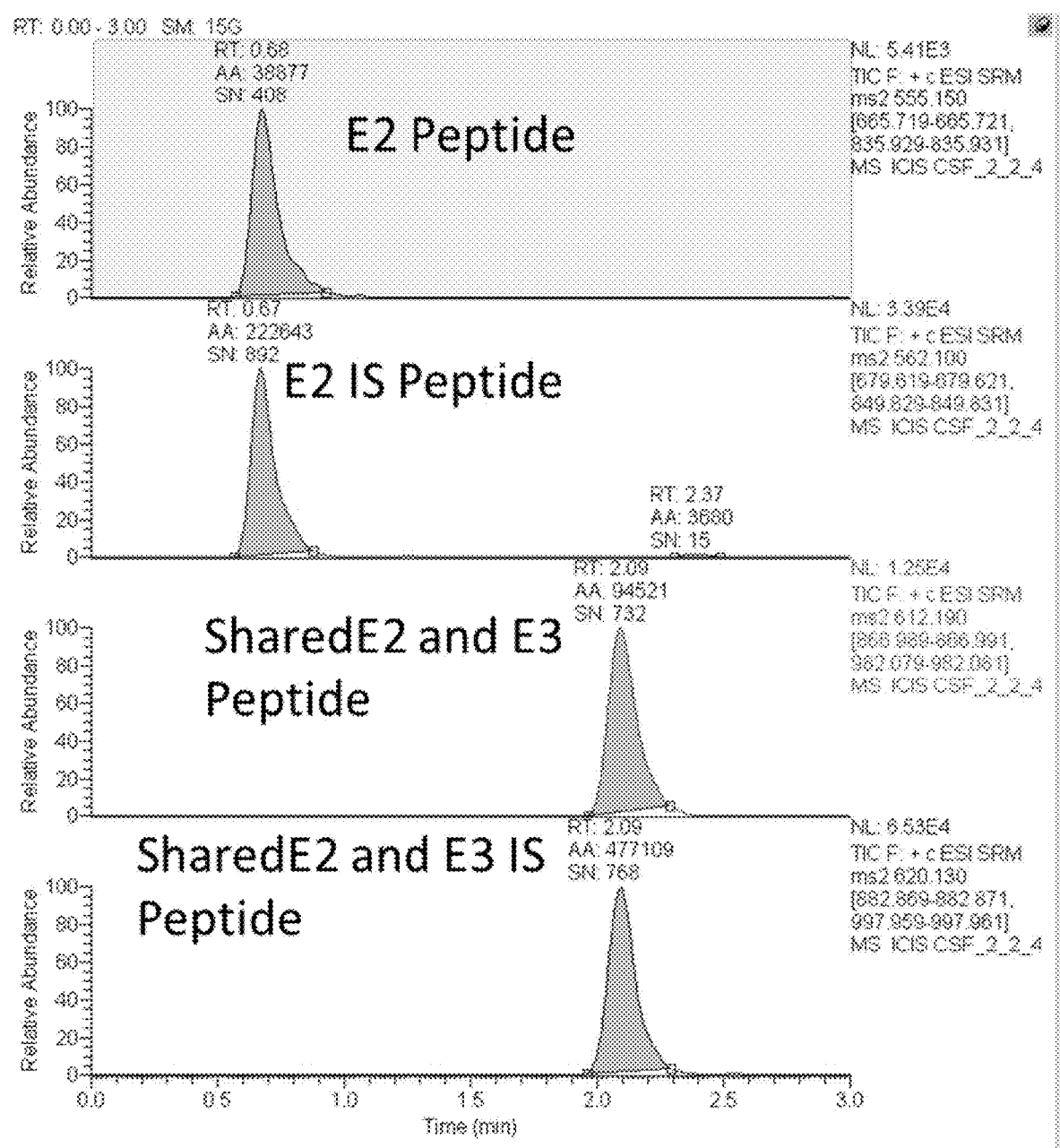
FIGS. 1A and 1B show example chromatograms of ApoE2/E2 phenotype which has a frequency of about 0.2%.
Figure 1B:
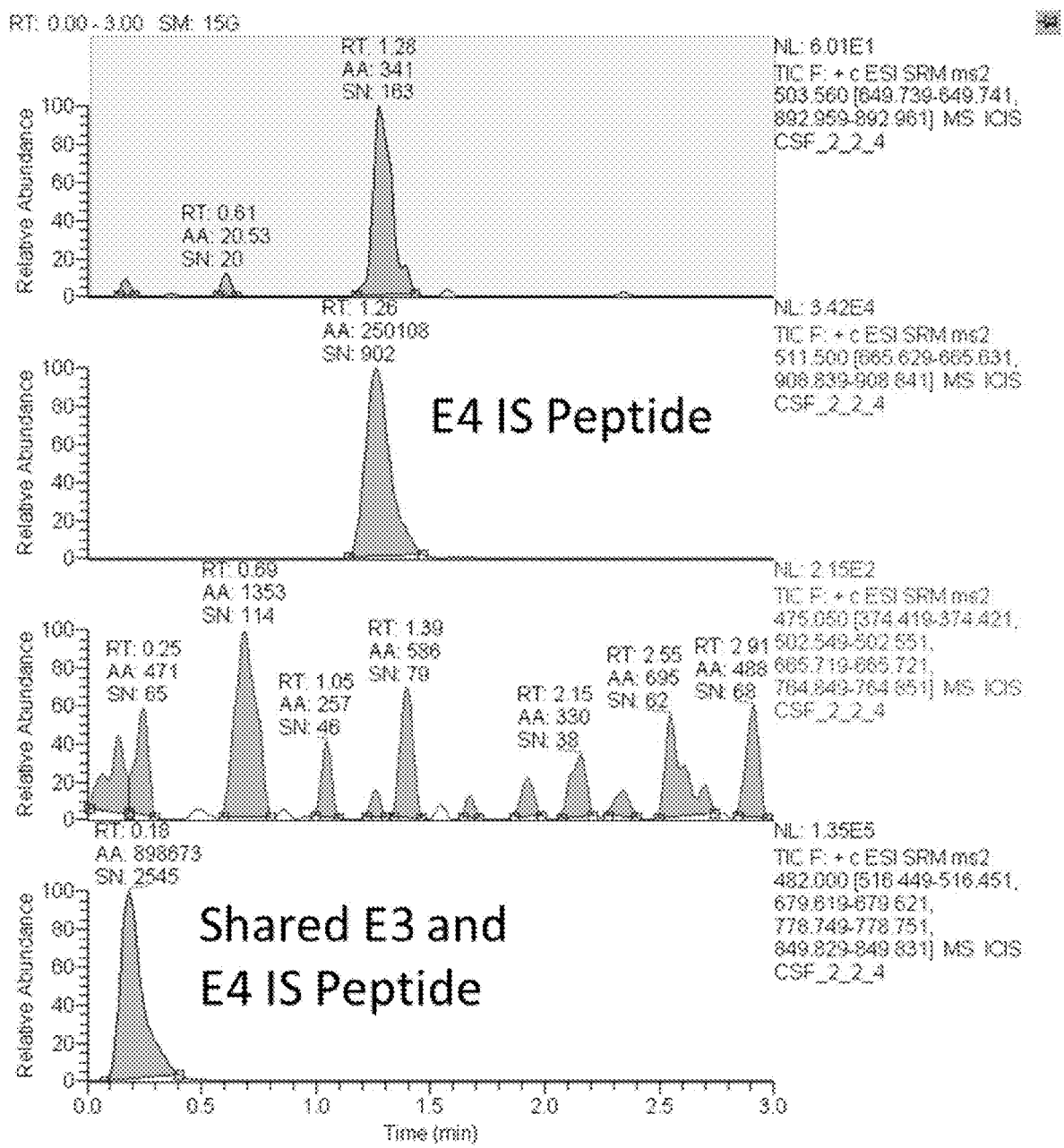
Figure 2A:
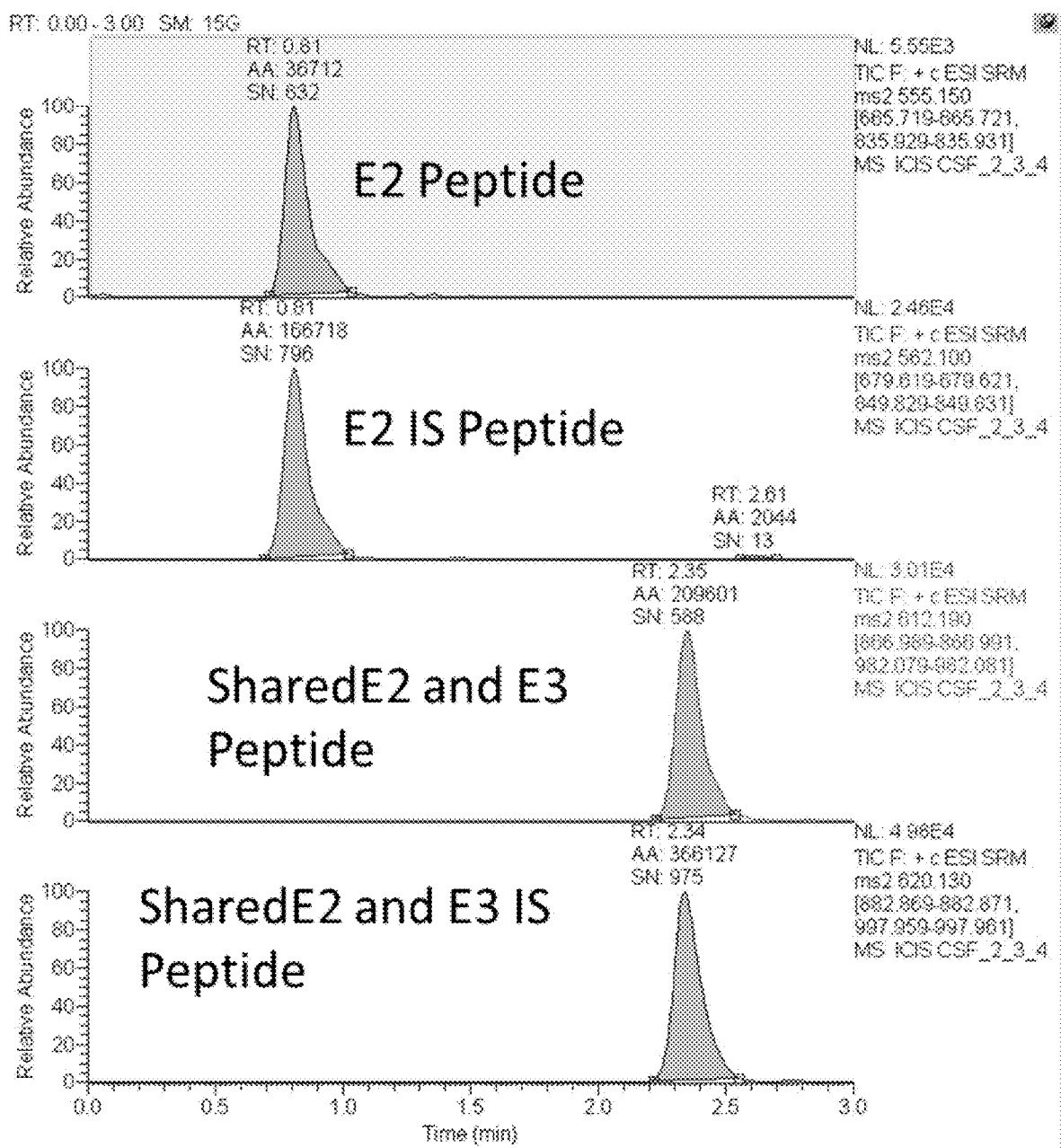
FIGS. 2A and 2B show example chromatograms of ApoE2/E3 phenotype which has a frequency of about 9.4%.
Figure 2B:
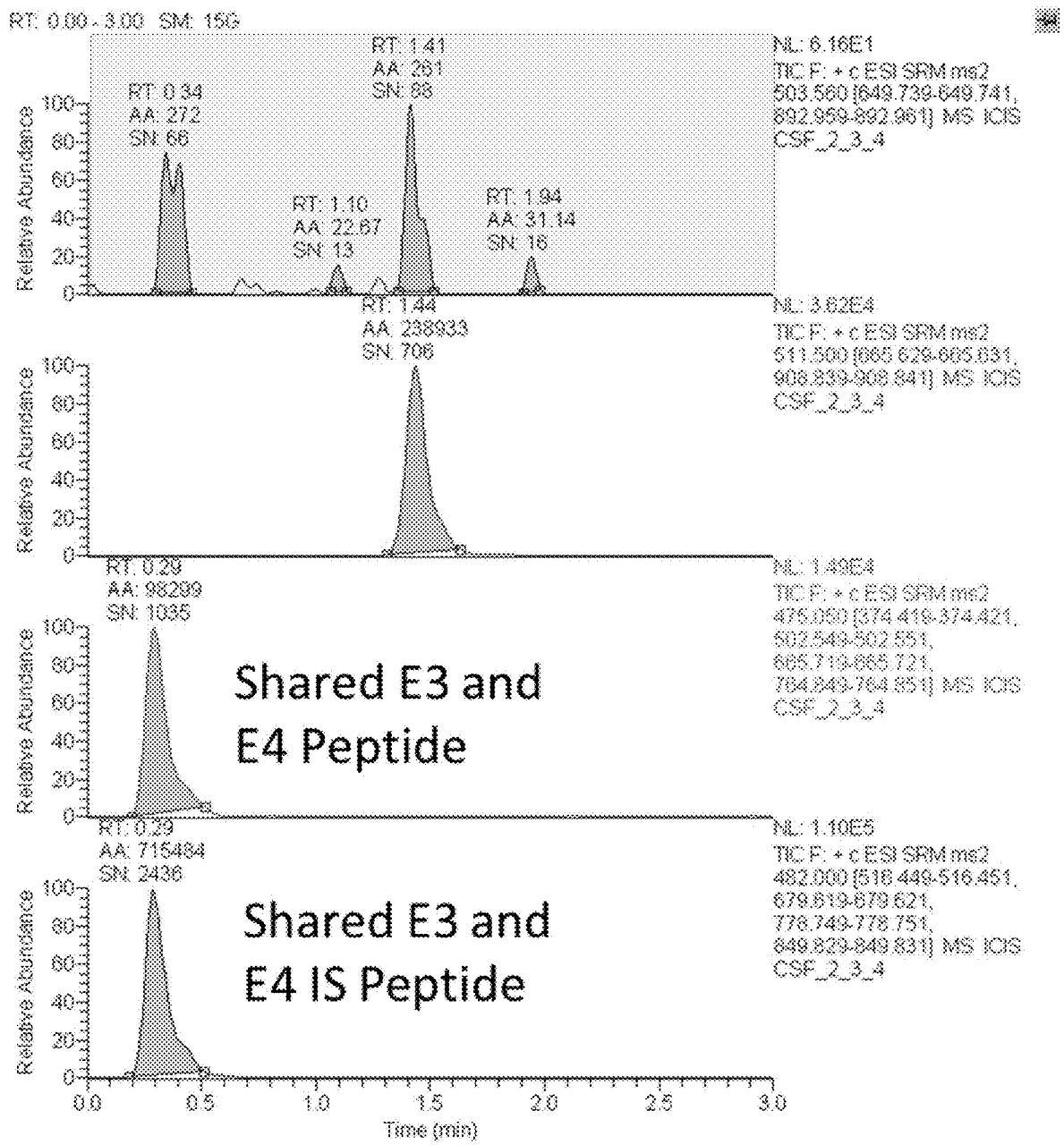
Figure 3A:
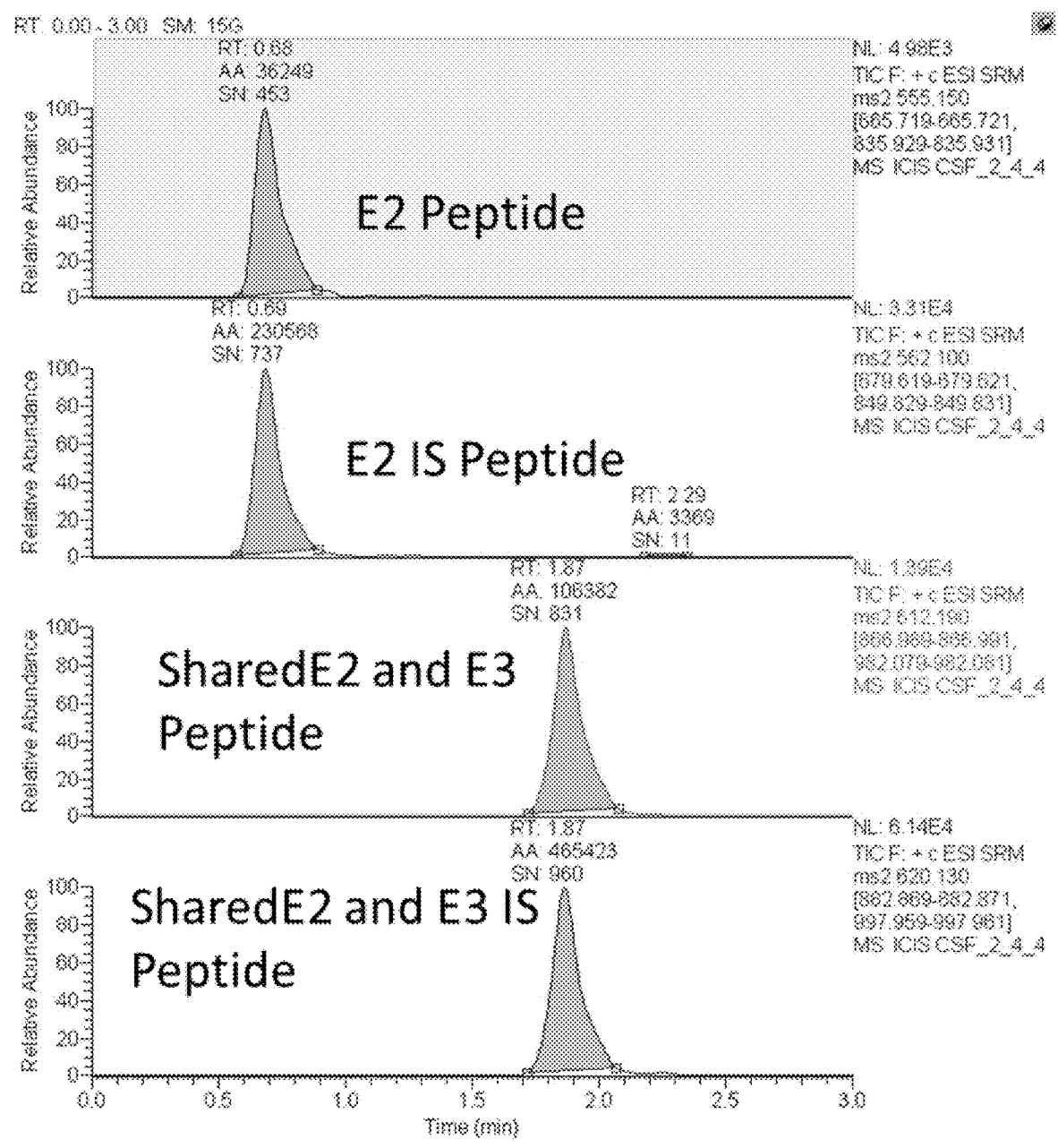
FIGS. 3A and 3B show example chromatograms of ApoE2/E4 phenotype which has a frequency of about 2.2%.
Figure 3B:
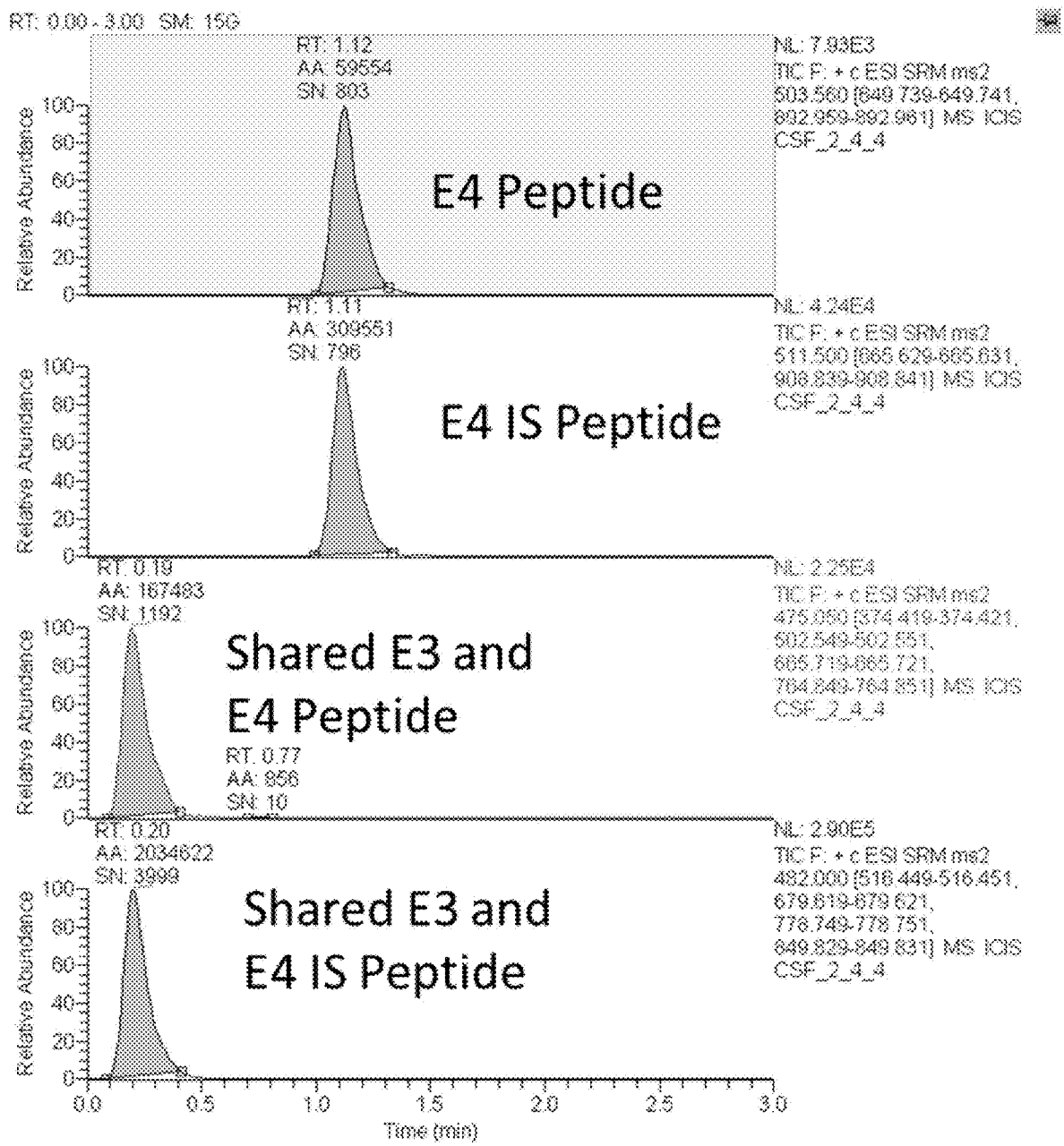
Figure 4A:
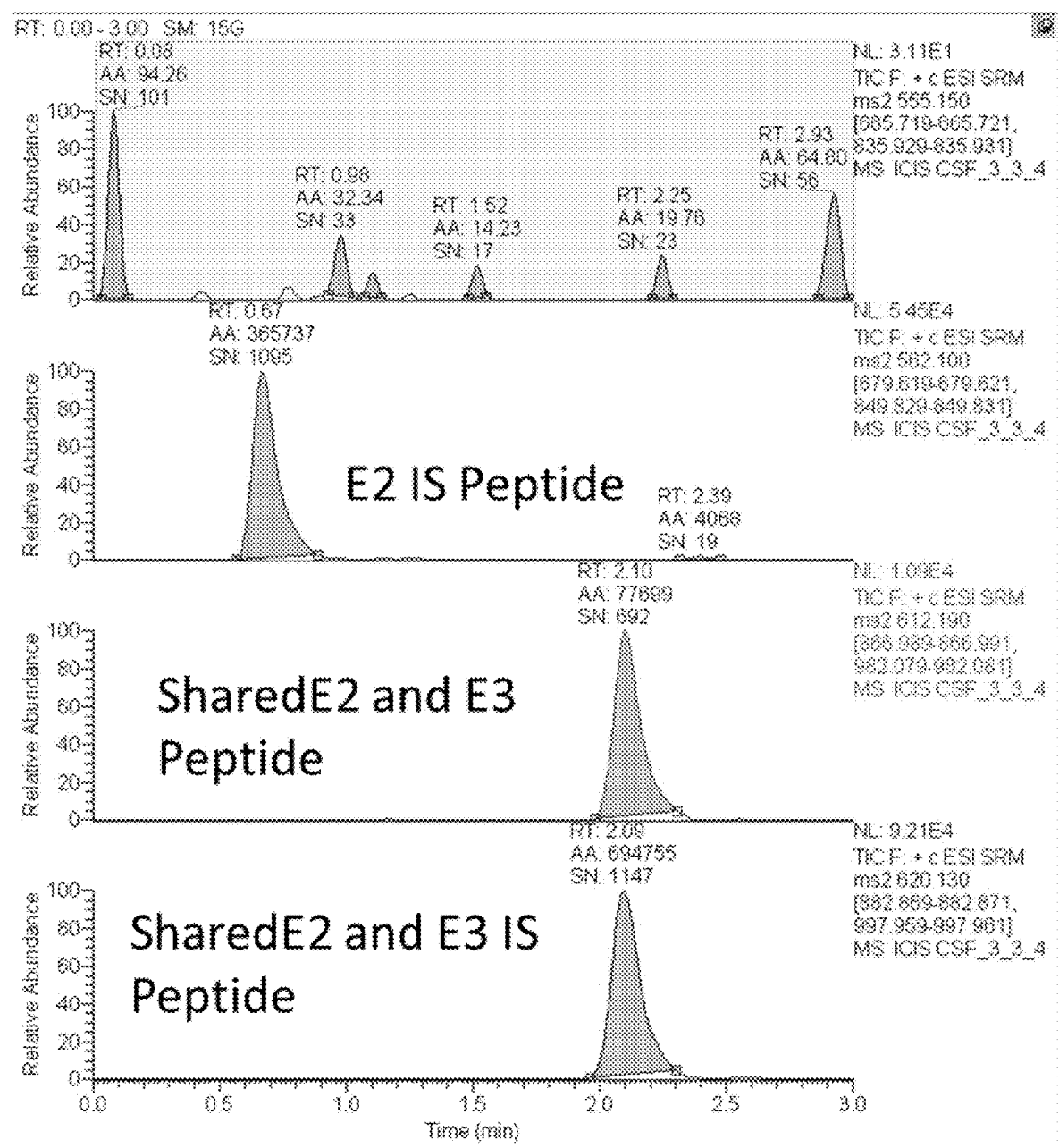
FIGS. 4A and 4B show example chromatograms of ApoE3/E3 phenotype which has a frequency of about 66%.
Figure 4B:
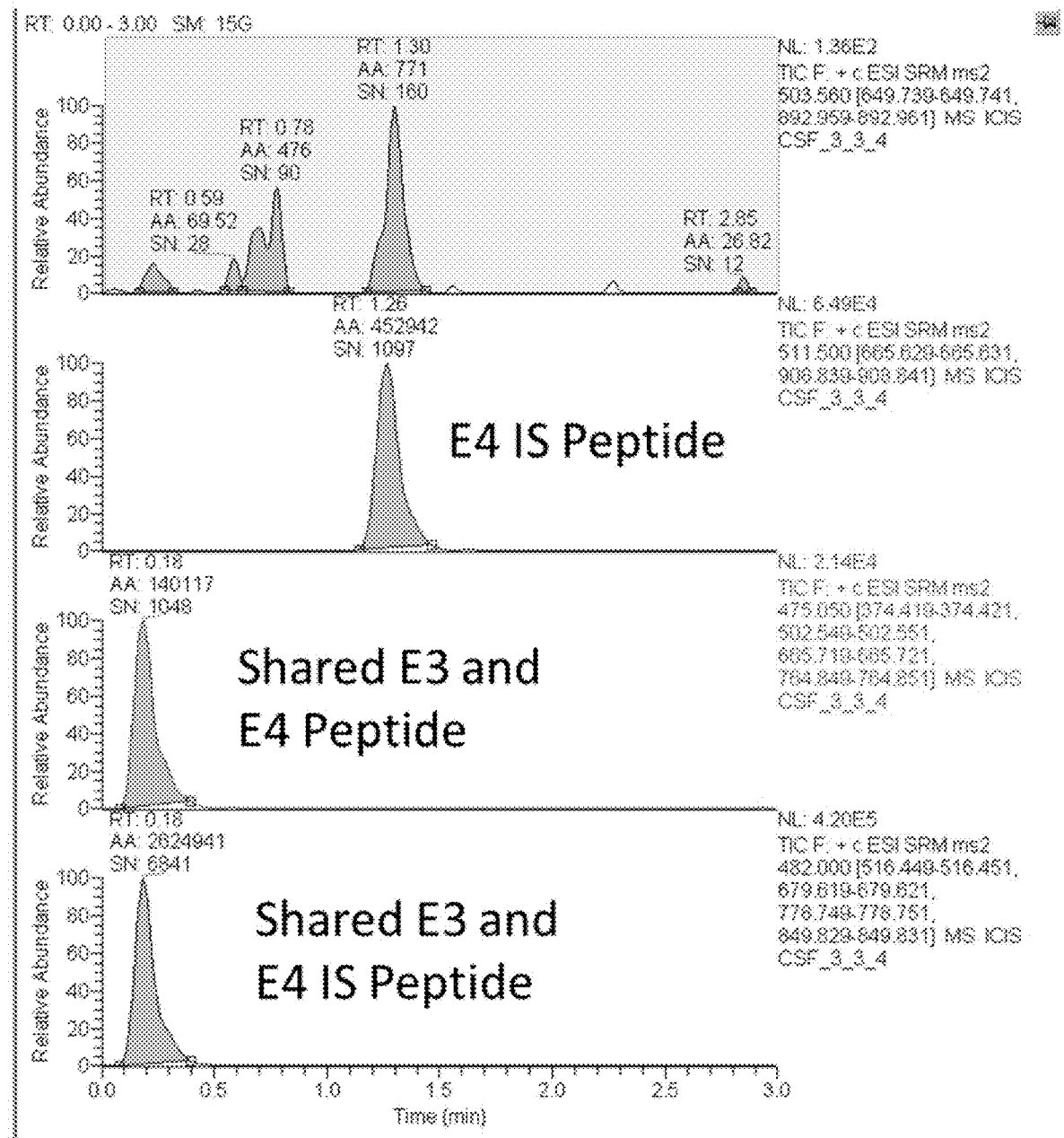
Figure 5A:
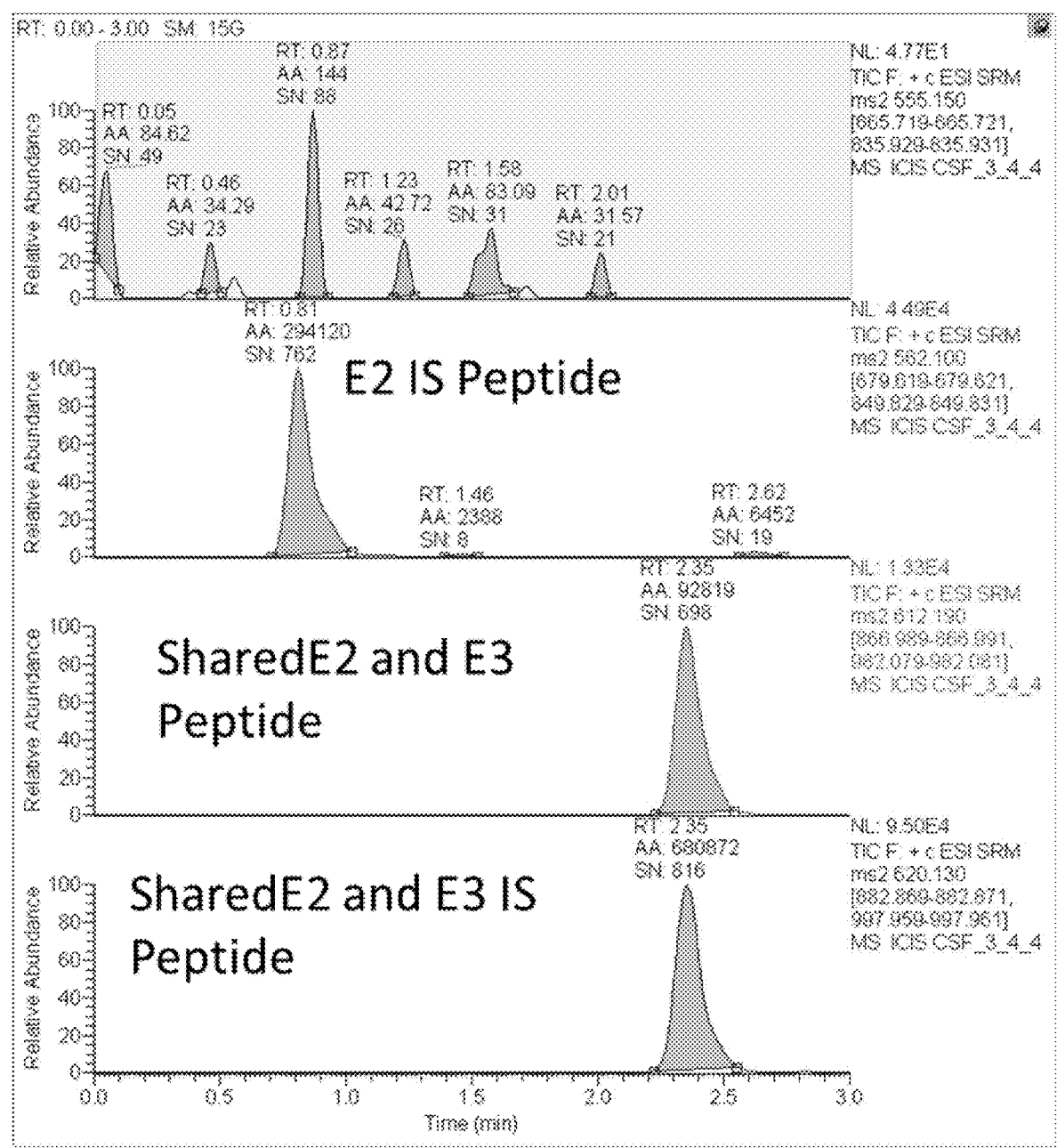
FIGS. 5A and 5B show example chromatograms of ApoE3/E4 phenotype which has a frequency of about 20%.
Figure 5B:
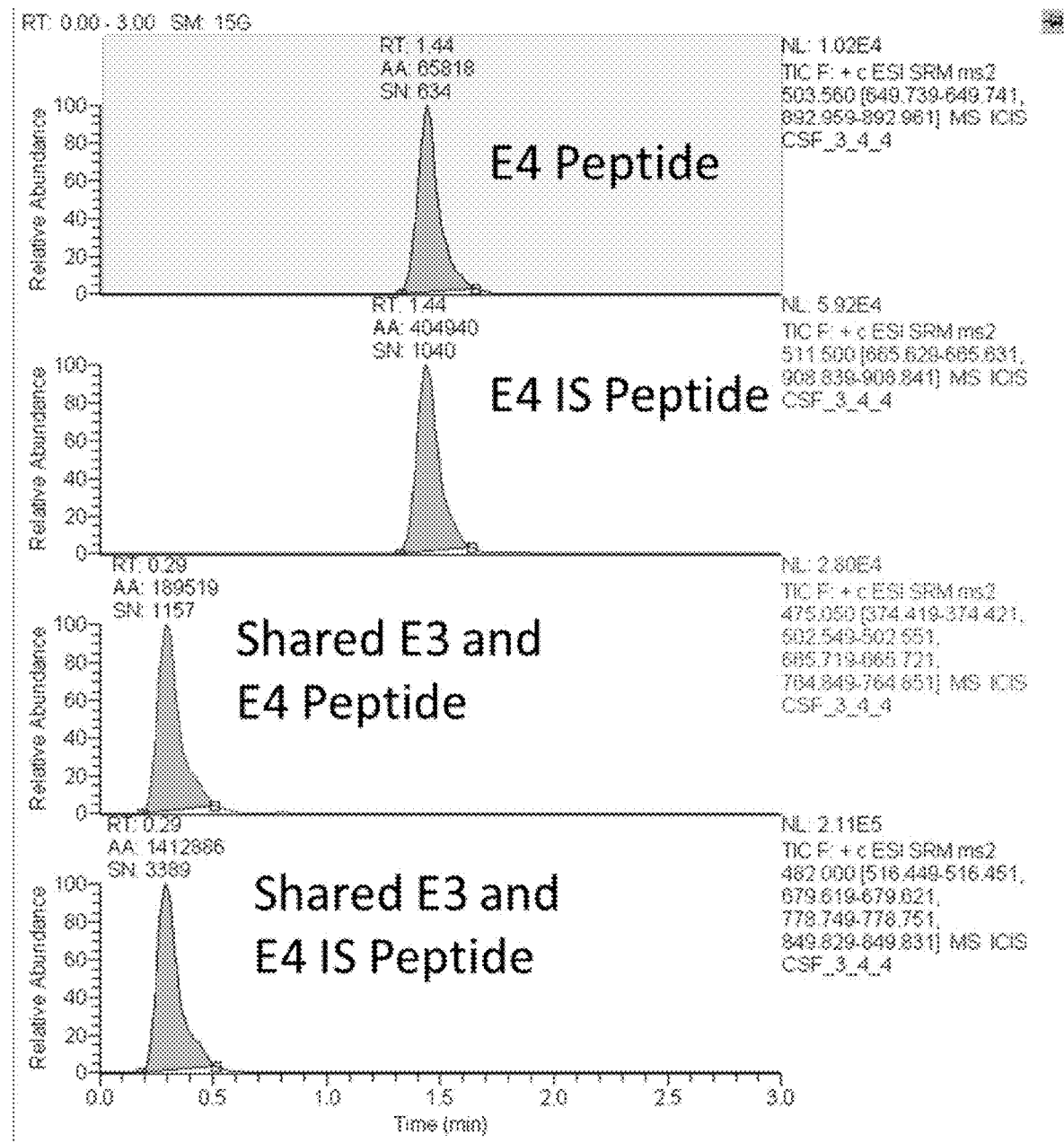
Figure 6A:
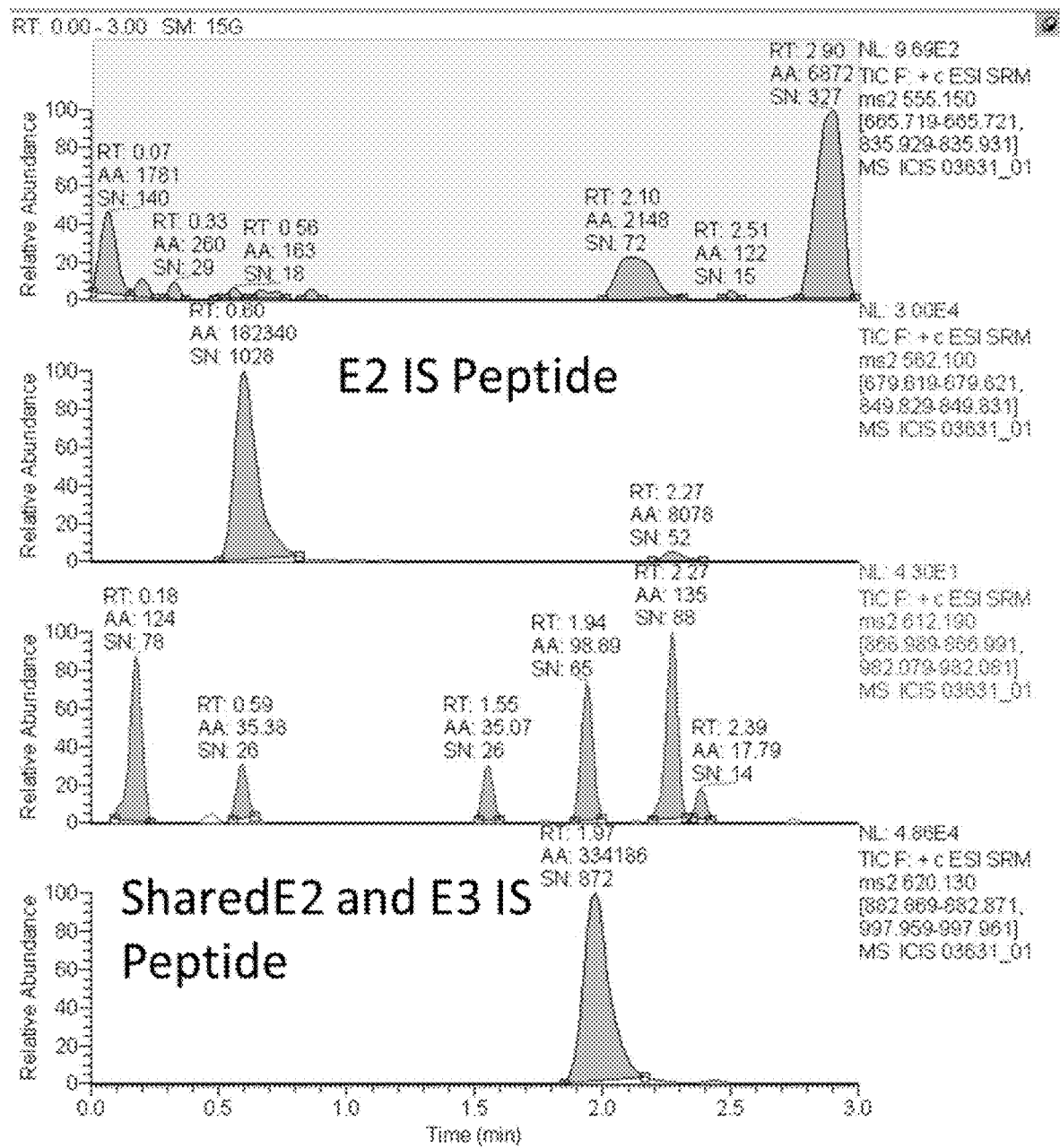
FIGS. 6A and 6B show example chromatograms of ApoE4/E4 phenotype which has a frequency of about 2.5%.
Figure 6B:
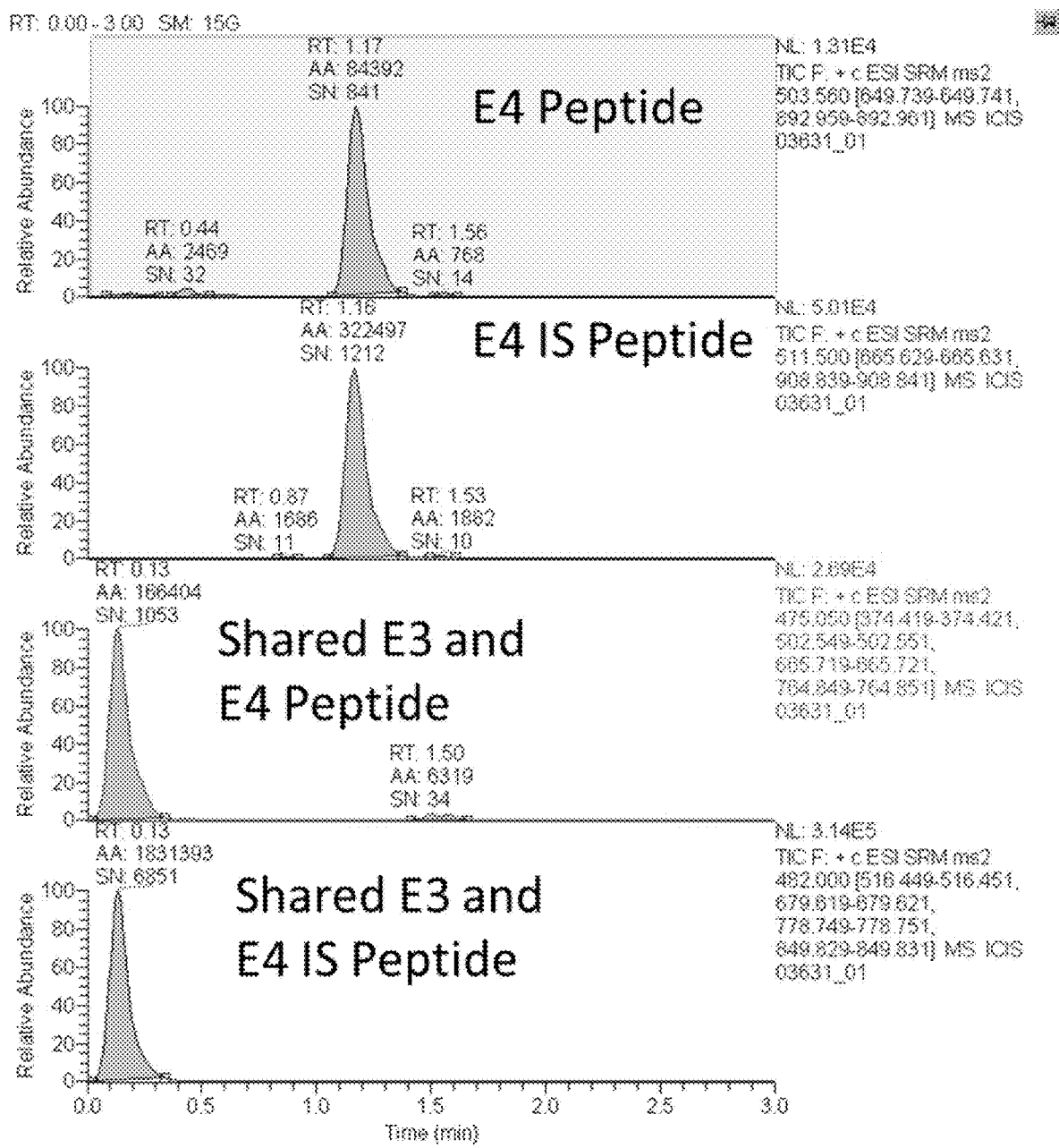
Figure 8A:
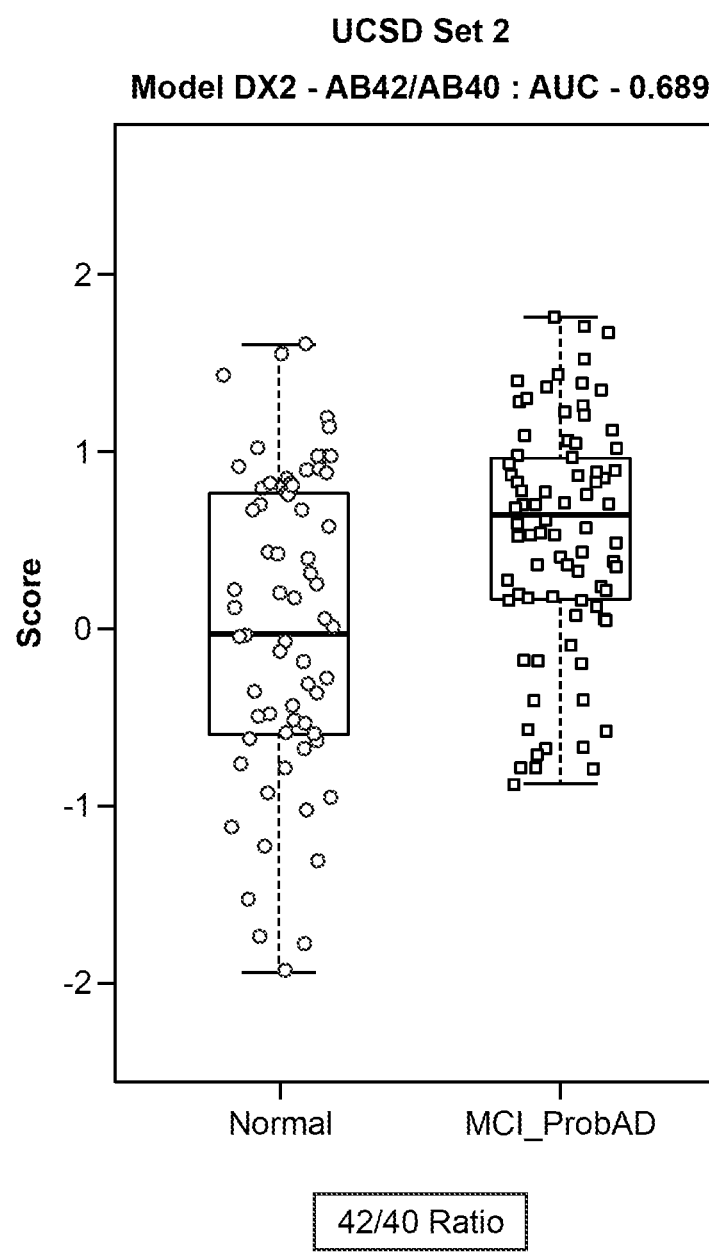
FIGS. 8A to 8C show the contribution of each Alzheimer's disease biomarker to the Risk Assessment Model. Formula for calculating the linear predictor (score) for MCI or Alzheimer's disease given: Aβ42 (pg/mL)/Aβ40 (pg/mL) ratio; ApoE4 allele count; Total ApoE (ug/mL). Score=2.8336−9.9026×Ratio+0.7358×ApoE4−0.2183×Total ApoE. Risk is categorized into three groups: Low risk; Average risk; High risk.
Figure 8B:
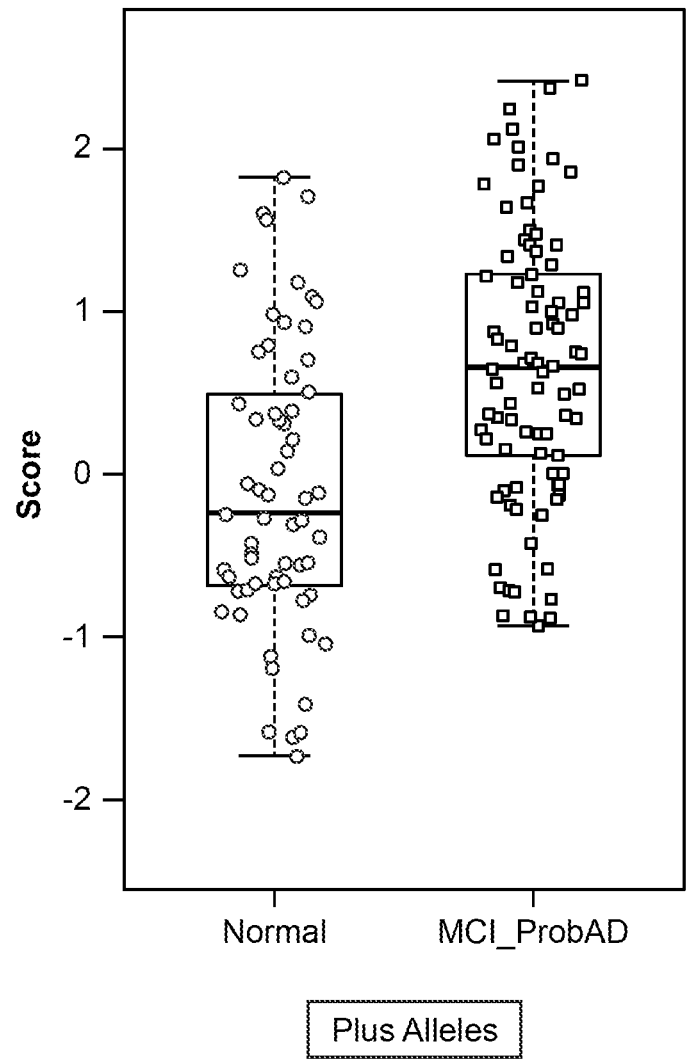
Figure 8C:
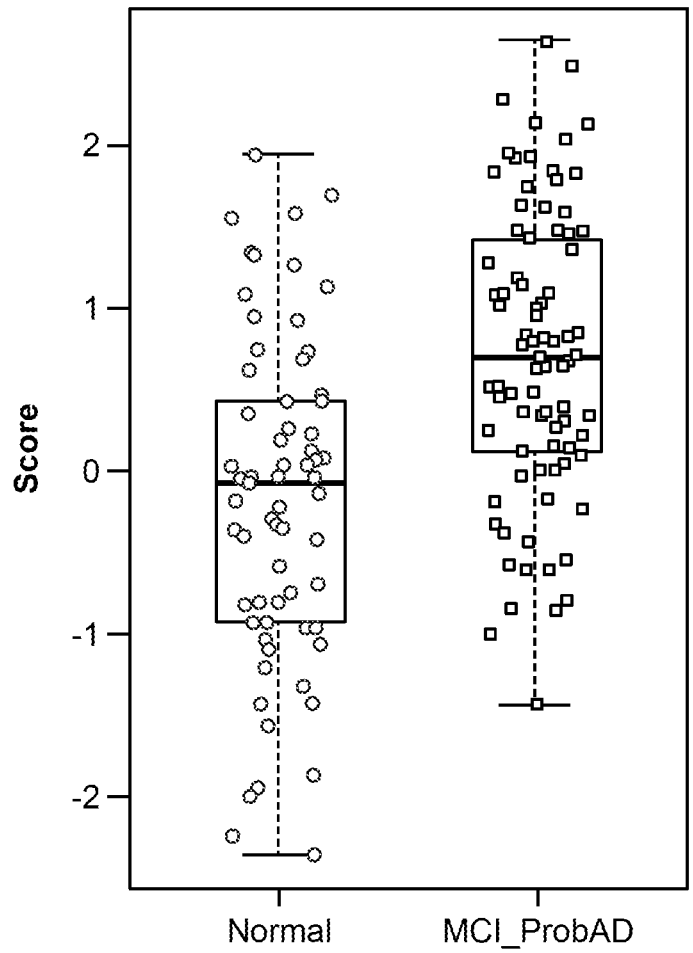
Figure 9A:
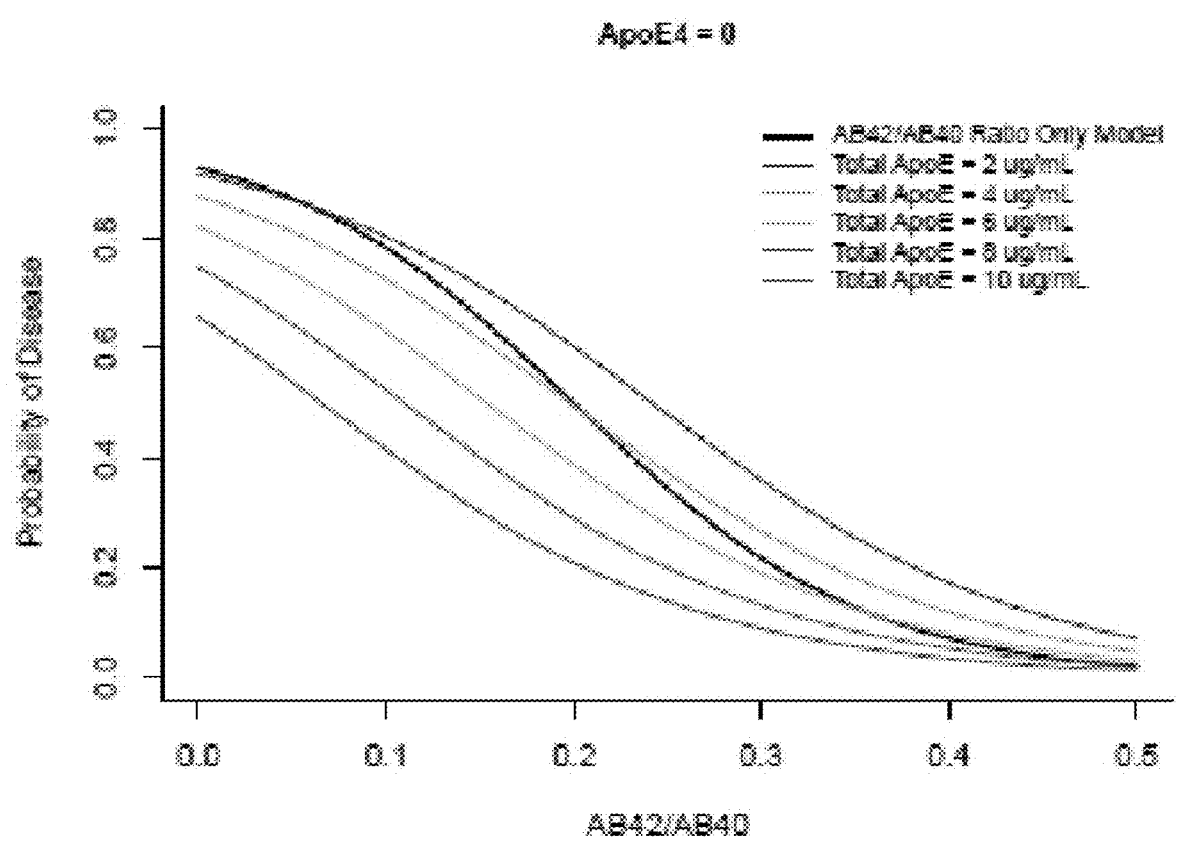
FIGS. 9A to 9C show the disease probability plots for Aβ42/40 ratio model vs. allele number.
Figure 9B:
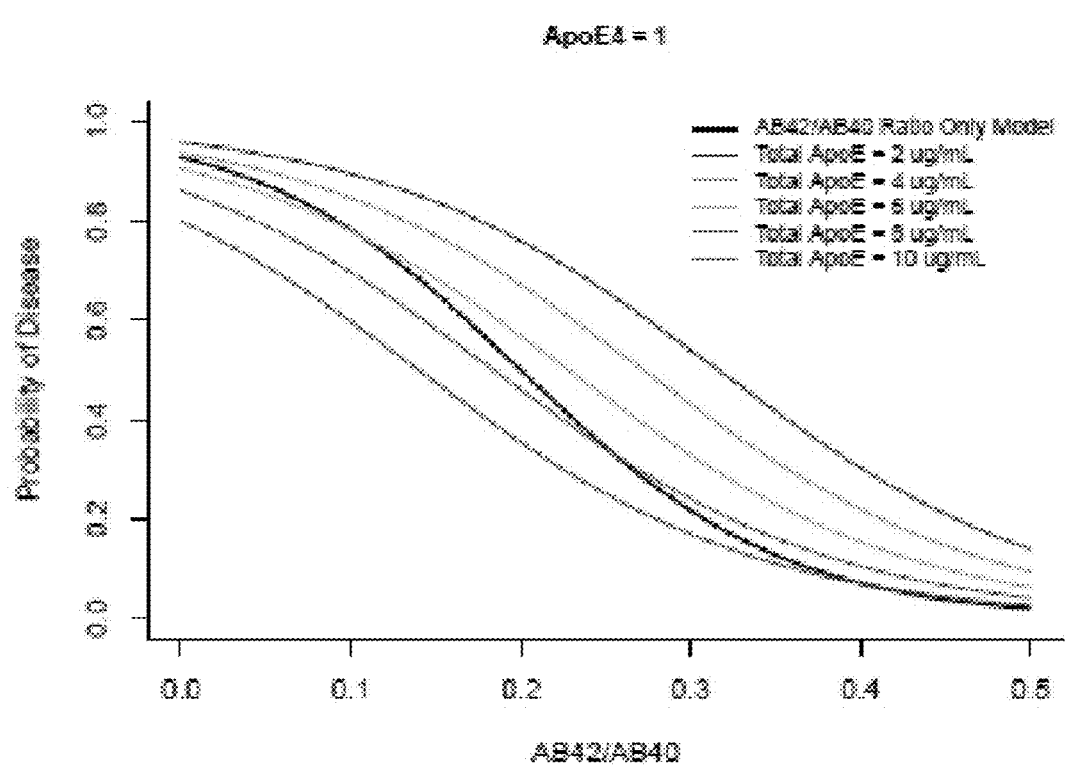
Figure 9C:
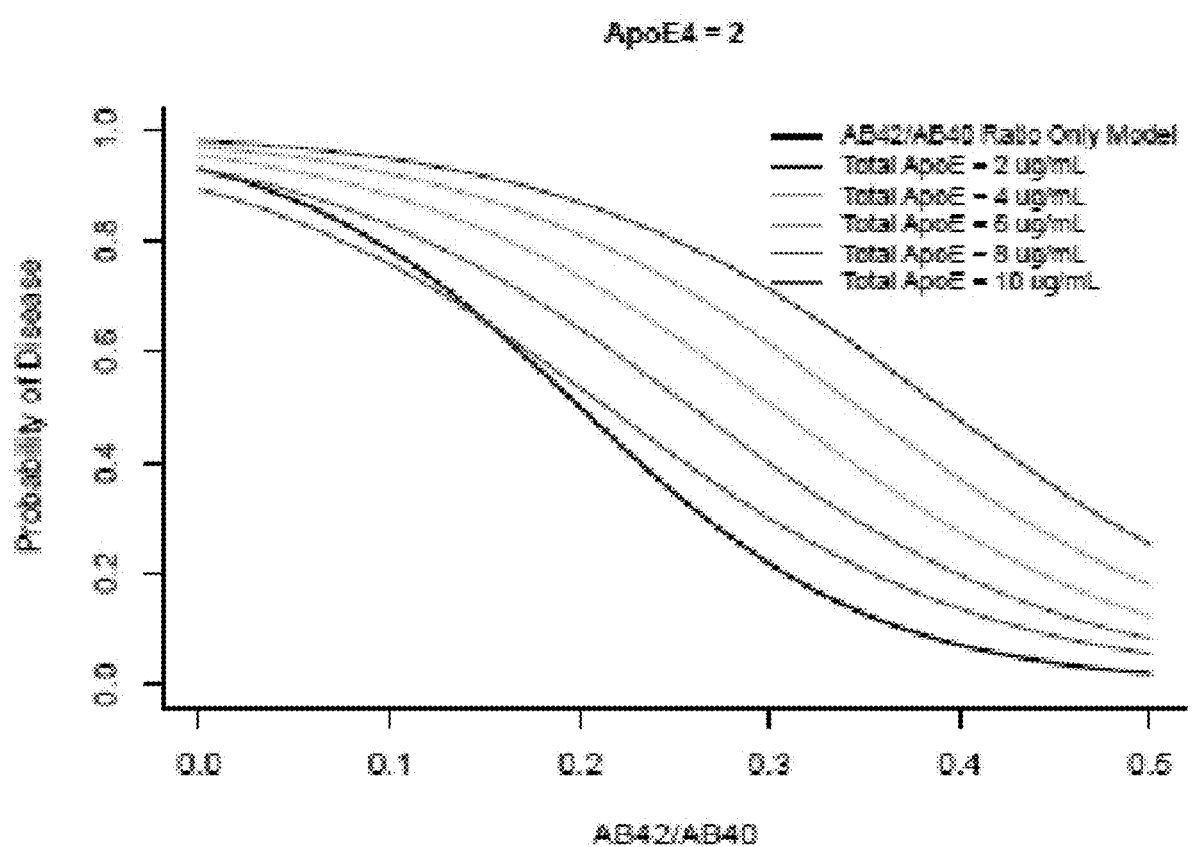
Figure 10A:
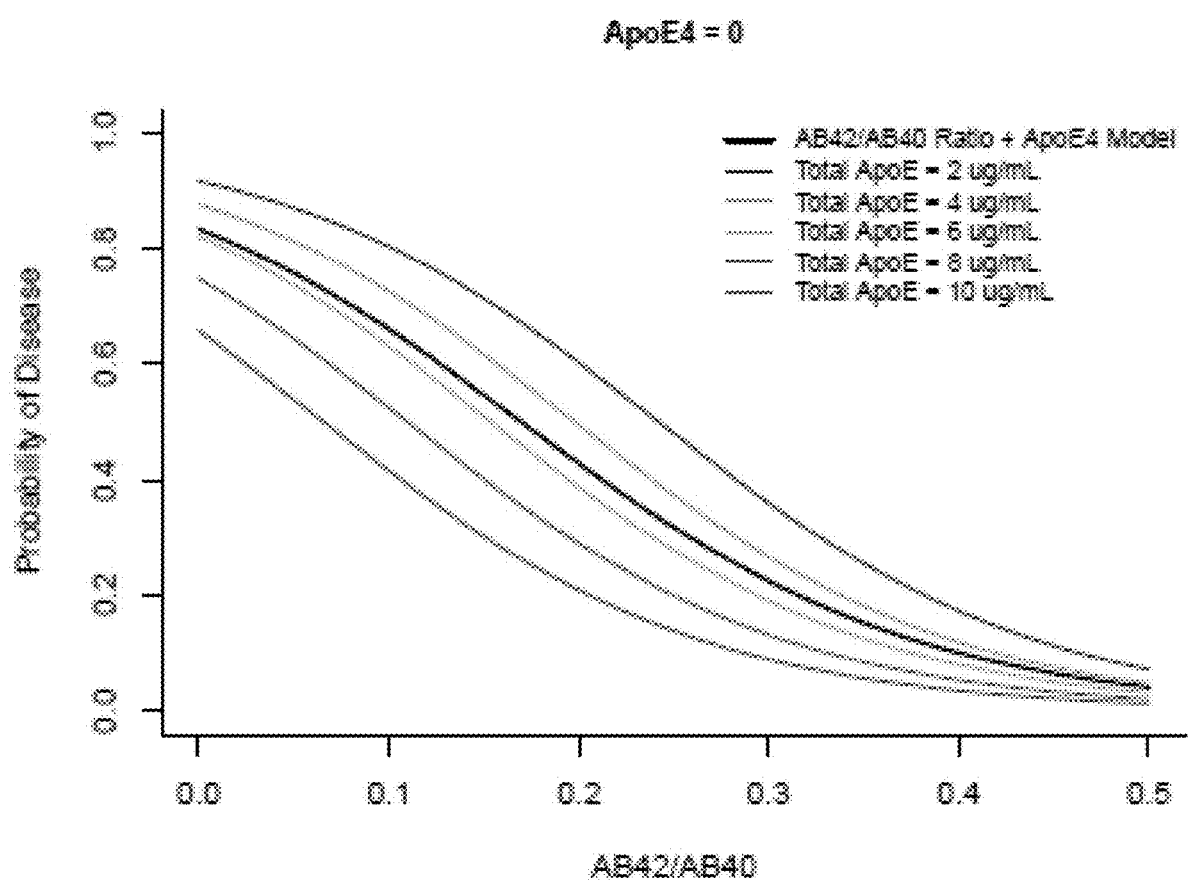
FIGS. 10A to 10C show the disease risk plots for Aβ42/40 ratio+total ApoE model vs. ApoE4 allele number.
Figure 10B:
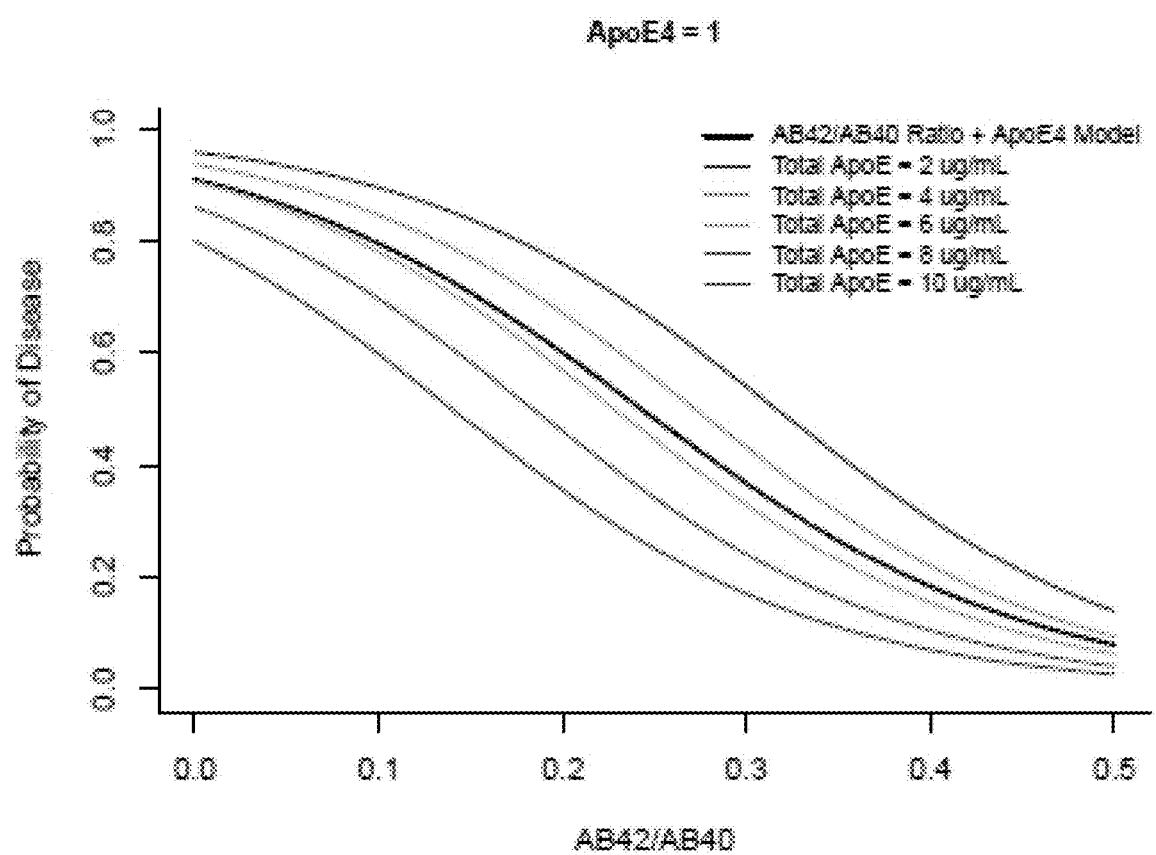
Figure 10C:
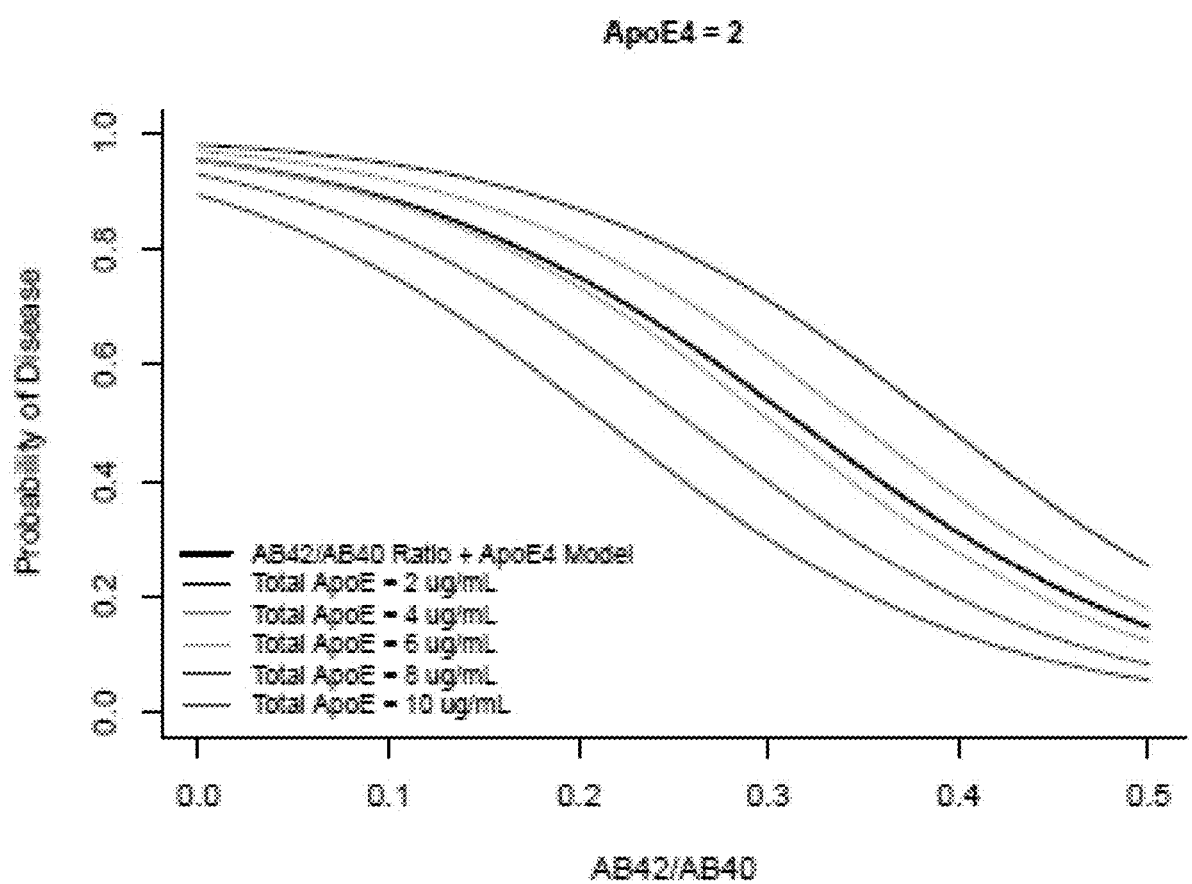
Figure 11:
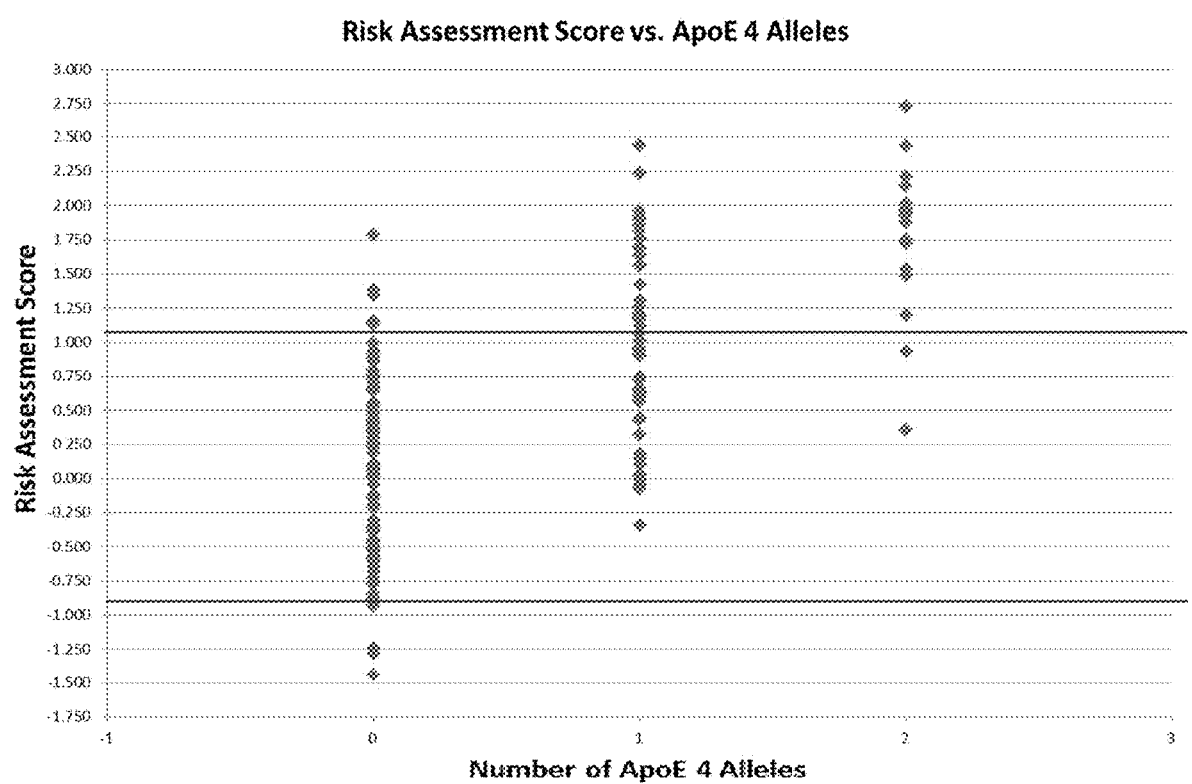
FIG. 11 shows the risk assessment score vs. number of ApoE4 alleles.
Figure 13:
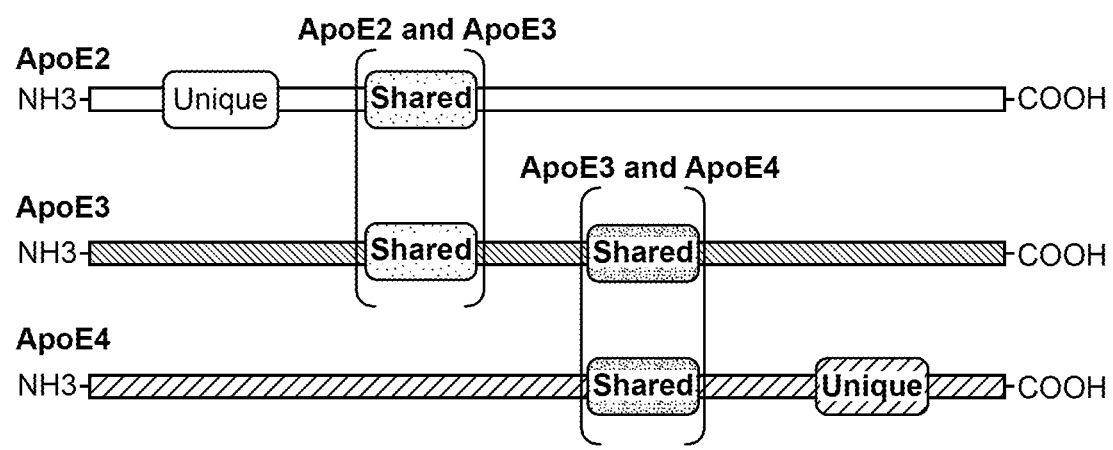
FIG. 13 shows a graphic representation of ApoE isotype phenotyping by mass spectrometry. ApoE2/E2 phenotype is determined by detecting an ion(s) associated with unique E2.

Apolipoprotein E (ApoE) is a well-defined genetic risk factor for late-onset Alzheimer disease (AD). The human APOE gene has three polymorphic alleles, ε2, ε3 and ε4 that result in six different phenotypes: ε2/ε2, ε2/ε3, ε3/ε3, ε2/ε4, ε3/ε4 and ε4/ε4. About half of AD patients carry the ε4 allele (compared with 14% in the general population), with the majority being heterozygotes (ε3/ε4). The number of inherited ε4 alleles is associated with both increased disease risk and decreased average age of onset compared with inheritance of the ε2 or ε3 alleles. The differences between the three ApoE isoforms are based on two amino acids that affect its structure and hence the interaction and binding of the protein with various lipids and beta-amyloid (Aβ). ApoE and Aβ can co-localize in the brain, and therefore their complementary roles in AD have been studied extensively. Circulating plasma and CSF ApoE levels were recently found to be potential biomarkers for AD. In addition, increased CSF Apo-E2 or -E3 levels might represent a protective response to injury in AD and may have neuroprotective effects by decreasing neuronal damage independent of tau and amyloid deposition in addition to its effects on amyloid clearance. Lower ApoE levels may also be associated with multiple sclerosis and other neurodegenerative diseases that affect brain lipid metabolism.

In certain embodiments, the methods provided herein are for determining the apolipoprotein E (ApoE) phenotype in a sample, said method comprising: (a) purifying ApoE in the sample; (b) ionizing ApoE in the sample to produce one or more ion(s) of ApoE; (c) detecting the ion(s) from step (b) by mass spectrometry; wherein the ApoE allele(s) present in the sample is determined from the identity of the ions detected in step (c).

In some embodiments, purifying provided herein comprises liquid chromatography. In some embodiments, the liquid chromatography comprises high performance liquid chromatography (HPLC).

In some embodiments, purifying provided herein comprises solid phase extraction (SPE).

In some embodiments, the ionization comprises electrospray ionization (ESI). In some embodiments, the ionization comprises ionizing in positive mode. In some embodiments, the ionization comprises ionizing in negative mode.

In some embodiments, methods provided herein further comprise adding an internal standard. In some embodiments, the internal standard is isotopically labeled.

In some embodiments, the phenotype determined by the method provided herein is ApoE2/ApoE2. In some embodiments, the phenotype is ApoE2/ApoE3. In some embodiments, the phenotype is ApoE2/ApoE4. In some embodiments, the phenotype is ApoE3/ApoE3. In some embodiments, the phenotype is ApoE3/ApoE4. In some embodiments, the phenotype is ApoE4/ApoE4.

In some embodiments, the presence of ApoE4 allele indicates increased risk of developing Alzheimer's disease. In some embodiments, the presence of ApoE4/ApoE4 alleles indicates increased risk of developing Alzheimer's disease.

In certain embodiments, the limit of quantitation of the methods is less than or equal to 10 ng/mL. In some embodiments, the limit of quantitation of the methods is less than or equal to 5 ng/mL. In some embodiments, the limit of quantitation of the methods is less than or equal to 4 ng/mL. In some embodiments, the limit of quantitation of the methods is less than or equal to 3 ng/mL. In some embodiments, the limit of quantitation of the methods is less than or equal to 2 ng/mL. In some embodiments, the limit of quantitation of the methods is less than or equal to 1 ng/mL. In some embodiments, the limit of quantitation of the methods is less than or equal to 0.5 ng/ml. In some embodiments, the limit of quantitation of the methods is less than or equal to 0.2 ng/ml. In some embodiments, the limit of quantitation of the methods is less than or equal to 0.1 ng/mL.

In some embodiments, the limit of detection of the methods is less than or equal to 5 ng/mL. In some embodiments, the limit of detection of the methods is less than or equal to 1 ng/mL. In some embodiments, the limit of detection of the methods is less than or equal to 0.5 ng/mL. In some embodiments, the limit of detection of the methods is less than or equal to 0.1 ng/mL. In some embodiments, the limit of detection of the methods is less than or equal to 0.05 ng/mL. In some embodiments, the limit of detection of the methods is less than or equal to 0.01 ng/mL.

In some embodiments, ApoE is not derivatized prior to mass spectrometry.

In some embodiments, ApoE is derivatized prior to mass spectrometry.

In certain embodiments, the sample is a body fluid. In some embodiments, the sample is cerebrospinal fluid (CSF). In some embodiments, the sample is plasma or serum. In some embodiments, the sample is whole blood. In some embodiments, the sample is saliva or urine.

In some embodiments, the methods may include adding an agent to the sample in an amount sufficient to deproteinate the sample.

Suitable test samples include any test sample that may contain the analyte of interest. In some preferred embodiments, a sample is a biological sample; that is, a sample obtained from any biological source, such as an animal, a cell culture, an organ culture, etc. In certain preferred embodiments samples are obtained from a mammalian animal, such as a dog, cat, horse, etc. Particularly preferred mammalian animals are primates, most preferably male or female humans. Particularly preferred samples include blood, plasma, serum, hair, muscle, urine, saliva, tear, cerebrospinal fluid, or other tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum.

Sample Preparation for Mass Spectrometry

Methods that may be used to enrich in ApoE relative to other components in the sample (e.g. protein) include for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Protein precipitation is one preferred method of preparing a test sample. Such protein purification methods are well known in the art, for example, Polson et al., *Journal of Chromatography B* 785:263-275 (2003), describes protein precipitation techniques suitable for use in the methods. Protein precipitation may be used to remove most of the protein from the sample leaving ApoE in the supernatant. The samples may be centrifuged to separate the liquid supernatant from the precipitated proteins. The resultant supernatant may then be applied to liquid chromatography and subsequent mass spectrometry analysis. In certain embodiments, the use of protein precipitation such as for example, acetonitrile protein precipitation, obviates the need for high turbulence liquid chromatography (HTLC) or other on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography (HTLC).

In some preferred embodiments, HPLC, alone or in combination with one or more purification methods, may be used to purify ApoE prior to mass spectrometry. In such embodiments samples may be extracted using an HPLC extraction cartridge which captures the analyte, then eluted and chromatographed on a second HPLC column or onto an analytical HPLC column prior to ionization. Because the steps involved in these chromatography procedures can be linked in an automated fashion, the requirement for operator involvement during the purification of the analyte can be minimized. This feature can result in savings of time and costs, and eliminate the opportunity for operator error.

It is believed that turbulent flow, such as that provided by HTLC columns and methods, may enhance the rate of mass transfer, improving separation characteristics. HTLC columns separate components by means of high chromatographic flow rates through a packed column containing rigid particles. By employing high flow rates (e.g., 3-5 mL/min), turbulent flow occurs in the column that causes nearly complete interaction between the stationary phase and the analyte(s) of interest. An advantage of using HTLC columns is that the macromolecular build-up associated with biological fluid matrices is avoided since the high molecular weight species are not retained under the turbulent flow conditions. HTLC methods that combine multiple separations in one procedure lessen the need for lengthy sample preparation and operate at a significantly greater speed. Such methods also achieve a separation performance superior to laminar flow (HPLC) chromatography. HTLC allows for direct injection of biological samples (plasma, urine, etc.). Direct injection is difficult to achieve in traditional forms of chromatography because denatured proteins and other biological debris quickly block the separation columns. HTLC also allows for very low sample volume of less than 1 mL, preferably less than 0.5 mL, preferably less than 0.2 mL, preferably. 1 mL.

Examples of HTLC applied to sample preparation prior to analysis by mass spectrometry have been described elsewhere. Sec, e.g., Zimmer et al., *J. Chromatogr.* A 854:23-35 (1999); see also, U.S. Pat. Nos. 5,968,367; 5,919,368; 5,795,469; and 5,772,874. In certain embodiments of the method, samples are subjected to protein precipitation as described above prior to loading on the HTLC column; in alternative preferred embodiments, the samples may be loaded directly onto the HTLC without being subjected to protein precipitation. The HTLC extraction column is preferably a large particle column. In various embodiments, one of more steps of the methods may be performed in an on-line, automated fashion. For example, in one embodiment, steps (i)-(v) are performed in an on-line, automated fashion. In another, the steps of ionization and detection are performed on-line following steps (i)-(v).

Liquid chromatography (LC) including high-performance liquid chromatography (HPLC) relies on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples but a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described for using HPLC for sample clean-up prior to mass spectrometry analysis. Sec, e.g., Taylor et al., *Therapeutic Drug Monitoring* 22:608-12 (2000); and Salm et al., *Clin. Therapeutics* 22 Supl. B:B71-B85 (2000).

One of skill in the art may select HPLC instruments and columns that are suitable for use with ApoE. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, the HTLC may be followed by HPLC on a hydrophobic column chromatographic system. In certain preferred embodiments, a TurboFlow Cyclone P® polymer-based column from Cohesive Technologies (60 μm particle size, 50×1.0 mm column dimensions, 100 Å pore size) is used. In related preferred embodiments, a Synergi Polar-RP® ether-linked phenyl, analytical column from Phenomenex Inc (4 μm particle size, 150×2.0 mm column dimensions, 80 Å pore size) with hydrophilic endcapping is used. In certain preferred embodiments, HTLC and HPLC are performed using HPLC Grade Ultra Pure Water and 100% methanol as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In certain preferred embodiments, ApoE or fragments thereof in a sample may be purified prior to ionization. In particularly preferred embodiments the chromatography is not gas chromatography.

Detection and Quantitation by Mass Spectrometry

In various embodiments, ApoE or fragments thereof may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, ApoE or a fragment thereof is ionized by heated electrospray ionization (HESI) in positive or negative mode. In alternative embodiments, ApoE or a fragment thereof is ionized by electrospray ionization (ESI) or atmospheric pressure chemical ionization (APCI) in positive or negative mode.

After the sample has been ionized, the positively charged or negatively charged ions thereby created may be analyzed to determine a mass-to-charge ratio. Suitable analyzers for determining mass-to-charge ratios include quadrupole analyzers, ion traps analyzers, and time-of-flight analyzers. The ions may be detected using several detection modes. For example, selected ions may be detected i.e., using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of ApoE. Methods of generating and using such standard curves are well known in the art and one of ordinary skill is capable of selecting an appropriate internal standard. For example, an isotope of ApoE may be used as an internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In particularly preferred embodiments, ApoE is detected and/or quantified using MS/MS as follows. The samples are subjected to liquid chromatography, preferably HPLC, the flow of liquid solvent from the chromatographic column enters the heated nebulizer interface of an MS/MS analyzer and the solvent/analyte mixture is converted to vapor in the heated tubing of the interface. The analyte is ionized by the selected ionizer. The ions, e.g. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of ApoE. Precursor ions with the correct mass/charge ratios of ApoE are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions of ApoE are selected while other ions are eliminated.

The methods may involve MS/MS performed in either positive or negative ion mode. Using standard methods well known in the art, one of ordinary skill is capable of identifying one or more fragment ions of a particular precursor ion of ApoE that may be used for selection in quadrupole 3 (Q3).

If the precursor ion of ApoE includes an alcohol or amine group, fragment ions are commonly formed that represent dehydration or deamination of the precursor ion, respectfully. In the case of precursor ions that include an alcohol group, such fragment ions formed by dehydration are caused by a loss of one or more water molecules from the precursor ion (i.e., where the difference in mass to charge ratio between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in mass to charge ratio between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (i.e., where the difference in mass to charge ratio between the precursor ion and fragment ion is about 35 for the loss of one water molecule and the loss of one ammonia molecule). Generally, the fragment ions that represent dehydrations or deaminations of the precursor ion are not specific fragment ions for a particular analyte. Accordingly, in preferred embodiments of the invention, MS/MS is performed such that at least one fragment ion of ApoE is detected that does not represent only a loss of one or more water molecules and/or a loss of one or more ammonia molecules from the precursor ion.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of ApoE. As described above, the relative abundance of a given ion may be converted into an absolute amount of the original analyte, using calibration standard curves based on peaks of one or more ions of an internal molecular standard.

The following examples serve to illustrate the invention. These examples are in no way intended to limit the scope of the methods.

EXAMPLES

Example 1: ApoE Phenotype Determination by Mass Spectrometry

Reagent Summary:

TABLE 1

| Reagents | Supplier & Catalog Number | Quantity |
|---|---|---|
| Apolipoprotein E2 | Abcam, 30R-AA019 | 0.5 mg |
| Apolipoprotein E3 | Abcam, 30R-2382 | 0.5 mg |
| Apolipoprotein E4 | Abcam, 003002 | 0.5 mg |
| Formic Acid | Millipore, FX0440-S | 1 L |
| Water | Burdick & Jackson, 365-4 | 4 L |
| Acetonitrile | Burdick & Jackson, 015-4 | 4 L |
| Sodium Deoxycholate | Fisher Scientific, PI89905 | 25 g |
| Dithiothreitol | Sigma, 43819-25G | 25 gg |
| Iodoacetamide | Sigma, I1149-25G | 25 g |
| Trypsin | Sigma, T1426-100MG | 0.5 mg |
| Apolipoprotein E2 IS | New England Peptide, Custom Synthesis | 2 mg |
| Apolipoprotein E2/3 IS | New England Peptide, Custom Synthesis | 2 mg |
| Apolipoprotein E3/4 IS | New England Peptide, Custom Synthesis | 2 mg |
| Apolipoprotein E4 IS | New England Peptide, Custom Synthesis | 2 mg |
| Apolipoprotein E total IS | New England Peptide, Custom Synthesis | 2 mg |
| Bovine Serum Albumin | Sigma, A2153-500G | 500 g |
| Phosphate Buffered Saline Tablets | Fisher, 003002 | 100 tablets |
| Ammonium Bicarbonate (AmBic) | Sigma, A6141-500G | 500 g |

TABLE 1-continued

| Reagents | Supplier & Catalog Number | Quantity |
|---|---|---|
| Bovine Cerebrospinal Fluid (BCSF) | Bioreclaimation IVT, custom Not stripped, pooled | 250 mL |
| Methanol | Fisher Scientific, A454-4 | 4 L |
| Activated Charcoal | Fisher Scientific, AC134370025 | 2.5 kg |
| Agilent BondElut C18 25 mg | Agilent, A4960125 | 1 plate |
| Agilent Poroshell 120 Bonus RP 2.1 × 100 2.7 um | Agilent, 695768-901 | 1 column |

The Identification of CSF Apolipoprotein E (ApoE) Isoforms by LC-MS/MS assay measures three distinct isoforms for ApoE, which can then be used to infer a phenotype. There are three alleles that encode for the apolipoprotein E protein, ApoE2, ApoE3, and ApoE4, which are expressed codominantly yielding six unique phenotypes; ApoE2/E2, ApoE2/E3, ApoE2/E4, ApoE3/E3, ApoE3/E4, and ApoE4/E4.

In order to measure each ApoE phenotype, a tryptic protein digestion is performed and a unique peptide is used as a surrogate to identify each protein isoform. There is a unique peptide for both the ApoE2 isoform and the ApoE4 isoform. The ApoE3 isoform is determined by using a shared peptide between the ApoE2 and ApoE3 isoform, and a shared peptide between the ApoE3 and ApoE4 isoform. Internal standards for each isoform are spiked into each sample to serve as retention time reference points.

CSF ApoE samples are analyzed using tandem mass spectrometry with a Thermo Aria Cohesive TLX-4 high flow LC coupled with a Thermo Fisher Quantiva Triple Quadrupole mass spectrometer. The data is monitored by multiple reaction monitoring (MRM) and analyzed using Thermo Fisher LC Quan data analysis software.

All mass-to-charge ratios (m/z) that identify the various ApoE alleles are described in the figures and summarized in Table 2 below.

| Compound | Precursor (m/z) | Product (m/z) | Collision Energy (V) | RF Lens (V) |
|---|---|---|---|---|
| ApoE3/4: LAVYQAGAR | 475.05 | 374.42 | 21 | 55 |
| ApoE3/4: LAVYQAGAR | 475.05 | 502.55 | 21 | 55 |
| ApoE3/4 IS: LAVYQAGAR(13C, 15N) | 482 | 516.45 | 21 | 55 |
| ApoE3/4 IS: LAVYQAGAR(13C, 15N) | 482 | 679.62 | 21 | 55 |
| ApoE4: LGADMEDVR | 503.56 | 649.74 | 20 | 56 |
| ApoE4: LGADMEDVR | 503.56 | 892.96 | 19 | 56 |
| ApoE4 IS: LGADMEDVR(13C, 15N) | 511.5 | 665.63 | 20 | 56 |
| ApoE4 IS: LGADMEDVR(13C, 15N) | 511.5 | 908.84 | 20 | 56 |
| ApoE2: C[+57.1]LAVYQAGAR | 555.15 | 665.72 | 21 | 54 |
| ApoE2: C[+57.1]LAVYQAGAR | 555.15 | 835.93 | 21 | 54 |
| ApoE2 IS: C[+57.1]LAVYQAGAR(13C, 15N) | 562.1 | 679.62 | 21 | 54 |
| ApoE2 IS: C[+57.1]LAVYQAGAR(13C, 15N) | 562.1 | 849.83 | 21 | 54 |
| ApoE2/3: LGADMEDVC[+57.1]GR | 612.19 | 866.99 | 22 | 89 |
| ApoE2/3: LGADMEDVC[+57.1]GR | 612.19 | 982.08 | 22 | 89 |
| ApoE2/3: LGADMEDVC[+57.1]GR(13C, 15N) | 620.13 | 882.87 | 22 | 89 |
| ApoE2/3: LGADMEDVC[+57.1]GR(13C, 15N) | 620.13 | 997.96 | 22 | 89 |

Expected values: Apolipoprotein E in CSF: 2.84-7.24 ug/mL; Apolipoprotein E in Serum: 20.07-101.68 ug/mL.

Five technical replicates of each quality control level were run in order of low, medium and high over the course of five separate days.

CSF Low Quality Control: 1.2 ug/mL
Apolipoprotein E:
   MEAN: 1.16 to 1.37
   SD: 0.03 to 0.12%
   % CV: 2.27 to 10.35%
   % Recovery: 97.00 to 104.00%

CSF Medium Quality Control: 3.0 Ug/mL
Apolipoprotein E:
   MEAN: 2.68 to 3.37
   SD: 0.05 to 0.33%
   % CV: 1.74 to 10.59%
   % Recovery: 89.27 to 112.40%

CSF High Quality Control: 15.0 ug/mL
Apolipoprotein E:
   MEAN: 13.38 to 16.54
   SD: 0.40 to 1.65%
   % CV: 4.71 to 11.36%
   % Recovery: 89.20 to 110.29%

Accuracy: Twenty patient samples with known APOE genotypes (analysis method: restriction length polymorphism (RLPM)) were analyzed by LC-MS/MS. ApoE phenotypes were then compared to the known genotypes. There was 100% concordance between the genotype and phenotype for each patient sample as shown in Table 3 below.

|  | RLPM (Genotyping) | LC-MS/MS (Phenotyping) |
|---|---|---|
| Patient 1 | E3/E3 | E3/E3 |
| Patient 2 | E3/E3 | E3/E3 |
| Patient 3 | E3/E3 | E3/E3 |
| Patient 4 | E3/E4 | E3/E4 |
| Patient 5 | E3/E4 | E3/E4 |
| Patient 6 | E3/E3 | E3/E3 |
| Patient 7 | E2/E3 | E2/E3 |
| Patient 8 | E3/E4 | E3/E4 |
| Patient 9 | E3/E3 | E3/E3 |
| Patient 10 | E3/E3 | E3/E3 |
| Patient 11 | E3/E3 | E3/E3 |
| Patient 12 | E4/E4 | E4/E4 |
| Patient 13 | E3/E3 | E3/E3 |
| Patient 14 | E2/E4 | E2/E4 |
| Patient 15 | E3/E4 | E3/E4 |
| Patient 16 | E4/E4 | E4/E4 |
| Patient 17 | E3/E3 | E3/E3 |
| Patient 18 | E3/E3 | E3/E3 |
| Patient 19 | E3/E4 | E3/E4 |
| Patient 20 | E3/E4 | E3/E4 |

Freeze-Thaw Stability: Freeze thaw analysis was conducted by analyzing six spiked phenotpyes which were divided into four even aliquots. All four aliquots for each phenotype were frozen at −90 to −60° ° C. Aliquots two through four were thawed to ambient temperature of 18-25° C. and frozen, for one freeze-thaw. Aliquots three and four were thawed to ambient temperature of 18-25° C. and frozen, for two freeze-thaws. Aliquot four was then thawed to ambient temperature 18-25° C. and frozen, for three freeze-thaws.

All aliquots were thawed a final time to ambient temperature 18-25° C. and analyzed in technical triplicate. Freeze thaw analysis contains data across three freeze thaw cycles. ApoE phenotype has acceptable stability up to three freeze thaw cycles.

TABLE 4

|  | Baseline | 1 FT | 2 FT | 3 FT |
|---|---|---|---|---|
| Phenotype 1 |  |  |  |  |
| Run 1 | E2/E2 | E2/E2 | E2/E2 | E2/E2 |
| Run 2 | E2/E2 | E2/E2 | E2/E2 | E2/E2 |
| Run 3 | E2/E2 | E2/E2 | E2/E2 | E2/E2 |
| Accuracy | 100% | 100% | 100% | 100% |
| Phenotype 2 |  |  |  |  |
| Run 1 | E2/E3 | E2/E3 | E2/E3 | E2/E3 |
| Run 2 | E2/E3 | E2/E3 | E2/E3 | E2/E3 |
| Run 3 | E2/E3 | E2/E3 | E2/E3 | E2/E3 |
| Mean | 100% | 100% | 100% | 100% |
| Phenotype 3 |  |  |  |  |
| Run 1 | E2/E4 | E2/E4 | E2/E4 | E2/E4 |
| Run 2 | E2/E4 | E2/E4 | E2/E4 | E2/E4 |
| Run 3 | E2/E4 | E2/E4 | E2/E4 | E2/E4 |
| Mean | 100% | 100% | 100% | 100% |
| Phenotype 4 |  |  |  |  |
| Run 1 | E3/E3 | E3/E3 | E3/E3 | E3/E3 |
| Run 2 | E3/E3 | E3/E3 | E3/E3 | E3/E3 |
| Run 3 | E3/E3 | E3/E3 | E3/E3 | E3/E3 |
| Mean | 100% | 100% | 100% | 100% |
| Phenotype 5 |  |  |  |  |
| Run 1 | E3/E4 | E3/E4 | E3/E4 | E3/E4 |
| Run 2 | E3/E4 | E3/E4 | E3/E4 | E3/E4 |
| Run 3 | E3/E4 | E3/E4 | E3/E4 | E3/E4 |
| Mean | 100% | 100% | 100% | 100% |
| Phenotype 6 |  |  |  |  |
| Run 1 | E4/E4 | E4/E4 | E4/E4 | E4/E4 |
| Run 2 | E4/E4 | E4/E4 | E4/E4 | E4/E4 |
| Run 3 | E4/E4 | E4/E4 | E4/E4 | E4/E4 |
| Mean | 100% | 100% | 100% | 100% |

Extracted Sample Stability: Ten samples were analyzed the same day as sample extraction for a baseline value. The next day, the same samples were re-injected for analysis against the baseline values. This assay yields enough sample for two injections. ApoE shows extracted sample stability of at least 1 day at 2 to 8° C. in the C-stack of the CTC Autosampler.

TABLE 5

|  | Baseline | 1 Day Extracted Sample Stability | % Accuracy |
|---|---|---|---|
| Patient 1 | 3/4 | 3/4 | 100% |
| Patient 2 | 3/3 | 3/3 | 100% |
| Patient 3 | 3/4 | 3/4 | 100% |
| Patient 4 | 2/3 | 2/3 | 100% |
| Patient 5 | 3/4 | 3/4 | 100% |
| Patient 6 | 3/4 | 3/4 | 100% |
| Patient 7 | 3/3 | 3/3 | 100% |
| Patient 8 | 3/4 | 3/4 | 100% |
| Patient 9 | 3/4 | 3/4 | 100% |
| Patient 10 | 2/4 | 2/4 | 100% |

Room Temperature Stability: Samples are stable up to 7 days at 18 to 25° C.

TABLE 6

|  | Baseline | 1 Day | 3 Days | 5 Days | 7 Days |
|---|---|---|---|---|---|
| RT Phenotype 1 |  |  |  |  |  |
| Run 1 | E2/E2 | E2/E2 | E2/E2 | E2/E2 | E2/E2 |
| Run 2 | E2/E2 | E2/E2 | E2/E2 | E2/E2 | E2/E2 |
| Run 3 | E2/E2 | E2/E2 | E2/E2 | E2/E2 | E2/E2 |
| Accuracy | 100% | 100% | 100% | 100% | 100% |

TABLE 6-continued

|  | Baseline | 1 Day | 3 Days | 5 Days | 7 Days |
|---|---|---|---|---|---|
| RT Phenotype 2 | | | | | |
| Run 1 | E2/E3 | E2/E3 | E2/E3 | E2/E3 | E2/E3 |
| Run 2 | E2/E3 | E2/E3 | E2/E3 | E2/E3 | E2/E3 |
| Run 3 | E2/E3 | E2/E3 | E2/E3 | E2/E3 | E2/E3 |
| Accuracy | 100% | 100% | 100% | 100% | 100% |
| RT Phenotype 3 | | | | | |
| Run 1 | E2/E4 | E2/E4 | E2/E4 | E2/E4 | E2/E4 |
| Run 2 | E2/E4 | E2/E4 | E2/E4 | E2/E4 | E2/E4 |
| Run 3 | E2/E4 | E2/E4 | E2/E4 | E2/E4 | E2/E4 |
| Accuracy | 100% | 100% | 100% | 100% | 100% |
| RT Phenotype 4 | | | | | |
| Run 1 | E3/E3 | E3/E3 | E3/E3 | E3/E3 | E3/E3 |
| Run 2 | E3/E3 | E3/E3 | E3/E3 | E3/E3 | E3/E3 |
| Run 3 | E3/E3 | E3/E3 | E3/E3 | E3/E3 | E3/E3 |
| Accuracy | 100% | 100% | 100% | 100% | 100% |
| RT Phenotype 5 | | | | | |
| Run 1 | E3/E4 | E3/E4 | E3/E4 | E3/E4 | E3/E4 |
| Run 2 | E3/E4 | E3/E4 | E3/E4 | E3/E4 | E3/E4 |
| Run 3 | E3/E4 | E3/E4 | E3/E4 | E3/E4 | E3/E4 |
| Accuracy | 100% | 100% | 100% | 100% | 100% |
| RT Phenotype 6 | | | | | |
| Run 1 | E4/E4 | E4/E4 | E4/E4 | E4/E4 | E4/E4 |
| Run 2 | E4/E4 | E4/E4 | E4/E4 | E4/E4 | E4/E4 |
| Run 3 | E4/E4 | E4/E4 | E4/E4 | E4/E4 | E4/E4 |
| Accuracy | 100% | 100% | 100% | 100% | 100% |

Refrigerated Stability: Samples are stable up to 7 days at 2 to 8° C.

TABLE 7

|  | Baseline | 1 Day | 3 Days | 5 Days | 7 Days |
|---|---|---|---|---|---|
| 4° C. Phenotype 1 | | | | | |
| Run 1 | E2/E2 | E2/E2 | E2/E2 | E2/E2 | E2/E2 |
| Run 2 | E2/E2 | E2/E2 | E2/E2 | E2/E2 | E2/E2 |
| Run 3 | E2/E2 | E2/E2 | E2/E2 | E2/E2 | E2/E2 |
| Accuracy | 100% | 100% | 100% | 100% | 100% |
| 4° C. Phenotype 2 | | | | | |
| Run 1 | E2/E3 | E2/E3 | E2/E3 | E2/E3 | E2/E3 |
| Run 2 | E2/E3 | E2/E3 | E2/E3 | E2/E3 | E2/E3 |
| Run 3 | E2/E3 | E2/E3 | E2/E3 | E2/E3 | E2/E3 |
| Accuracy | 100% | 100% | 100% | 100% | 100% |
| 4° C. Phenotype 3 | | | | | |
| Run 1 | E2/E4 | E2/E4 | E2/E4 | E2/E4 | E2/E4 |
| Run 2 | E2/E4 | E2/E4 | E2/E4 | E2/E4 | E2/E4 |
| Run 3 | E2/E4 | E2/E4 | E2/E4 | E2/E4 | E2/E4 |
| Accuracy | 100% | 100% | 100% | 100% | 100% |
| 4° C. Phenotype 4 | | | | | |
| Run 1 | E3/E3 | E3/E3 | E3/E3 | E3/E3 | E3/E3 |
| Run 2 | E3/E3 | E3/E3 | E3/E3 | E3/E3 | E3/E3 |
| Run 3 | E3/E3 | E3/E3 | E3/E3 | E3/E3 | E3/E3 |
| Accuracy | 100% | 100% | 100% | 100% | 100% |
| 4° C. Phenotype 5 | | | | | |
| Run 1 | E3/E4 | E3/E4 | E3/E4 | E3/E4 | E3/E4 |
| Run 2 | E3/E4 | E3/E4 | E3/E4 | E3/E4 | E3/E4 |
| Run 3 | E3/E4 | E3/E4 | E3/34 | E3/E4 | E3/E4 |
| Accuracy | 100% | 100% | 100% | 100% | 100% |
| 4° C. Phenotype 6 | | | | | |
| Run 1 | E4/E4 | E4/E4 | E4/E4 | E4/E4 | E4/E4 |
| Run 2 | E4/E4 | E4/E4 | E4/E4 | E4/E4 | E4/E4 |
| Run 3 | E4/E4 | E4/E4 | E4/E4 | E4/E4 | E4/E4 |
| Accuracy | 100% | 100% | 100% | 100% | 100% |

Frozen Stability: Samples are stable for at least 31 days at −30 to −10° C.

TABLE 8

|  | Baseline | 1 Day | 3 Days | 5 Days | 7 Days | 14 Days | 21 Days | 31 Days |
|---|---|---|---|---|---|---|---|---|
| −20° C. Phenotype 1 | | | | | | | | |
| Run 1 | E2/E2 | E2/E2 | E2/E2 | E2/E2 | E2/E2 | E2/E2 | E2/E2 | E2/E2 |
| Run 2 | E2/E2 | E2/E2 | E2/E2 | E2/E2 | E2/E2 | E2/E2 | E2/E2 | E2/E2 |
| Run 3 | E2/E2 | E2/E2 | E2/E2 | E2/E2 | E2/E2 | E2/E2 | E2/E2 | E2/E2 |
| Accuracy | 100% | 100% | 100% | 100% | 100% | 100% | 100% | 100% |
| −20° C. Phenotype 2 | | | | | | | | |
| Run 1 | E2/E3 | E2/E3 | E2/E3 | E2/E3 | E2/E3 | E2/E3 | E2/E3 | E2/E3 |
| Run 2 | E2/E3 | E2/E3 | E2/E3 | E2/E3 | E2/E3 | E2/E3 | E2/E3 | E2/E3 |
| Run 3 | E2/E3 | E2/E3 | E2/E3 | E2/E3 | E2/E3 | E2/E3 | E2/E3 | E2/E3 |
| Accuracy | 100% | 100% | 100% | 100% | 100% | 100% | 100% | 100% |
| −20° C. Phenotype 3 | | | | | | | | |
| Run 1 | E2/E4 | E2/E4 | E2/E4 | E2/E4 | E2/E4 | E2/E4 | E2/E4 | E2/E4 |
| Run 2 | E2/E4 | E2/E4 | E2/E4 | E2/E4 | E2/E4 | E2/E4 | E2/E4 | E2/E4 |
| Run 3 | E2/E4 | E2/E4 | E2/E4 | E2/E4 | E2/E4 | E2/E4 | E2/E4 | E2/E4 |
| Accuracy | 10056 | 100% | 100% | 100% | 100% | 100% | 100% | 100% |
| −20° C. Phenotype 4 | | | | | | | | |
| Run 1 | E3/E3 | E3/E3 | E3/E3 | E3/E3 | E3/E3 | E3/E3 | E3/E3 | E3/E3 |
| Run 2 | E3/E3 | E3/E3 | E3/E3 | E3/E3 | E3/E3 | E3/E3 | E3/E3 | E3/E3 |
| Run 3 | E3/E3 | E3/E3 | E3/E3 | E3/E3 | E3/E3 | E3/E3 | E3/E3 | E3/E3 |
| Accuracy | 100% | 100% | 100% | 100% | 100% | 100% | 100% | 100% |

TABLE 8-continued

|  | Baseline | 1 Day | 3 Days | 5 Days | 7 Days | 14 Days | 21 Days | 31 Days |
|---|---|---|---|---|---|---|---|---|
| −20° C. Phenotype 5 | | | | | | | | |
| Run 1 | E3/E4 | E3/E4 | E3/E4 | E3/E4 | E3/E4 | E3/E4 | E3/E4 | E3/E4 |
| Run 2 | E3/E4 | E3/E4 | E3/E4 | E3/E4 | E3/E4 | E3/E4 | E3/E4 | E3/E4 |
| Run 3 | E3/E4 | E3/E4 | E3/E4 | E3/E4 | E3/E4 | E3/E4 | E3/E4 | E3/E4 |
| Accuracy | 100% | 100% | 100% | 100% | 100% | 100% | 100% | 100% |
| −20° C. Phenotype 6 | | | | | | | | |
| Run 1 | E4/E4 | E4/E4 | E4/E4 | E4/E4 | E4/E4 | E4/E4 | E4/E4 | E4/E4 |
| Run 2 | E4/E4 | E4/E4 | E4/E4 | E4/E4 | E4/E4 | E4/E4 | E4/E4 | E4/E4 |
| Run 3 | E4/E4 | E4/E4 | E4/E4 | E4/E4 | E4/E4 | E4/E4 | E4/E4 | E4/E4 |
| Accuracy | 100% | 100% | 100% | 100% | 100% | 100% | 100% | 100% |

Interference Study: Acceptability criteria: The difference due to a potential interfering substance should be ≤2SD or 20% CV to be considered acceptable.

Hemolysis Interference: Six patient pools were spiked with hemoglobin (Sigma Cat. #H7379) and analyzed in triplicate for a baseline, slight, moderate and gross hemolysis interference. A 10 mg/mL solution of hemoglobin was used for "gross" interference. The 10 mg/mL solution was diluted with 10 mM BS 1:10 and 1:20 for moderate and slight interference, respectively.

All levels of hemolysis are unacceptable due to the possible contamination of serum-derived Apolipoprotein E.

TABLE 9

| Hemolysis | | | | |
|---|---|---|---|---|
|  | Baseline | Lite | Moderate | Gross |
| 2/2 | | | | |
| Expected | 2/2 | 2/2 | 2/2 | 2/2 |
| Run 1 | 2/2 | 2/2 | 2/2 | 2/2 |
| Run 2 | 2/2 | 2/2 | 2/2 | 2/2 |
| Run 3 | 2/2 | 2/2 | 2/2 | 2/2 |
| Accuracy | 100% | 100% | 100% | 100% |
| 2/3 | | | | |
| Expected | 2/3 | 2/3 | 2/3 | 2/3 |
| Run 1 | 2/3 | 2/3 | 2/3 | 2/3 |
| Run 2 | 2/3 | 2/3 | 2/3 | 2/3 |
| Run 3 | 2/3 | 2/3 | 2/3 | 2/3 |
| Accuracy | 100% | 100% | 100% | 100% |
| 2/4 | | | | |
| Expected | 2/4 | 2/4 | 2/4 | 2/4 |
| Run 1 | 2/4 | 2/4 | 2/4 | 2/4 |
| Run 2 | 2/4 | 2/4 | 2/4 | 2/4 |
| Run 3 | 2/4 | 2/4 | 2/4 | 2/4 |
| Accuracy | 100% | 100% | 100% | 100% |
| 3/3 | | | | |
| Expected | 3/3 | 3/3 | 3/3 | 3/3 |
| Run 1 | 3/3 | 3/3 | 3/3 | 3/3 |
| Run 2 | 3/3 | 3/3 | 3/3 | 3/3 |
| Run 3 | 3/3 | 3/3 | 3/3 | 3/3 |
| Accuracy | 100% | 100% | 100% | 100% |
| 3/4 | | | | |
| Expected | 3/4 | 3/4 | 3/4 | 3/4 |
| Run 1 | 3/4 | 3/4 | 3/4 | 3/4 |
| Run 2 | 3/4 | 3/4 | 3/4 | 3/4 |
| Run 3 | 3/4 | 3/4 | 3/4 | 3/4 |
| Accuracy | 100% | 100% | 100% | 100% |

TABLE 9-continued

| Hemolysis | | | | |
|---|---|---|---|---|
|  | Baseline | Lite | Moderate | Gross |
| 4/4 | | | | |
| Expected | 4/4 | 4/4 | 4/4 | 4/4 |
| Run 1 | 4/4 | 4/4 | 4/4 | 4/4 |
| Run 2 | 4/4 | 4/4 | 4/4 | 4/4 |
| Run 3 | 4/4 | 4/4 | 4/4 | 4/4 |
| Accuracy | 100% | 100% | 100% | 100% |

Lipemia Interference: Six patient pools were spiked with intralipid (Sigma Cat. #I141) and analyzed in triplicate for a baseline, slight, moderate and gross lipemic interference. A 1:5 dilution (intralipid:10 mM PBS) was used for "gross" interference. The 1:5 solution was diluted with 10 mM PBS 1:10 and 1:20 for moderate and slight interference, respectively. ApoE is acceptable for all degrees of lipemia CSF samples.

TABLE 10

| Lipimic | | | | |
|---|---|---|---|---|
|  | Baseline | Lite | Moderate | Gross |
| 2/2 | | | | |
| Expected | 2/2 | 2/2 | 2/2 | 2/2 |
| Run 1 | 2/2 | 2/2 | 2/2 | 2/2 |
| Run 2 | 2/2 | 2/2 | 2/2 | 2/2 |
| Run 3 | 2/2 | 2/2 | 2/2 | 2/2 |
| Accuracy | 100% | 100% | 100% | 100% |
| 2/3 | | | | |
| Expected | 2/3 | 2/3 | 2/3 | 2/3 |
| Run 1 | 2/3 | 2/3 | 2/3 | 2/3 |
| Run 2 | 2/3 | 2/3 | 2/3 | 2/3 |
| Run 3 | 2/3 | 2/3 | 2/3 | 2/3 |
| Accuracy | 100% | 100% | 100% | 100% |
| 2/4 | | | | |
| Expected | 2/4 | 2/4 | 2/4 | 2/4 |
| Run 1 | 2/4 | 2/4 | 2/4 | 2/4 |
| Run 2 | 2/4 | 2/4 | 2/4 | 2/4 |
| Run 3 | 2/4 | 2/4 | 2/4 | 2/4 |
| Accuracy | 100% | 100% | 100% | 100% |
| 3/3 | | | | |
| Expected | 3/3 | 3/3 | 3/3 | 3/3 |
| Run 1 | 3/3 | 3/3 | 3/3 | 3/3 |
| Run 2 | 3/3 | 3/3 | 3/3 | 3/3 |
| Run 3 | 3/3 | 3/3 | 3/3 | 3/3 |
| Accuracy | 100% | 100% | 100% | 100% |

TABLE 10-continued

| | Lipimic | | | |
|---|---|---|---|---|
| | Baseline | Lite | Moderate | Gross |
| 3/4 | | | | |
| Expected | 3/4 | 3/4 | 3/4 | 3/4 |
| Run 1 | 3/4 | 3/4 | 3/4 | 3/4 |
| Run 2 | 3/4 | 3/4 | 3/4 | 3/4 |
| Run 3 | 3/4 | 3/4 | 3/4 | 3/4 |
| Accuracy | 100% | 100% | 100% | 100% |
| 4/4 | | | | |
| Expected | 4/4 | 4/4 | 4/4 | 4/4 |
| Run 1 | 4/4 | 4/4 | 4/4 | 4/4 |
| Run 2 | 4/4 | 4/4 | 4/4 | 4/4 |
| Run 3 | 4/4 | 4/4 | 4/4 | 4/4 |
| Accuracy | 100% | 100% | 100% | 100% |

Bilirubin Interference: Six patient pools were spiked with bilirubin (Sigma Cat. #B4126) and analyzed in triplicate for a baseline, slight, moderate and gross icteric interference. A 1 mg/mL solution of bilirubin was used for "gross" interference. The 1 mg/mL solution was diluted with 10 mM PBS 1:10 and 1:20 for moderate and slight interference, respectively. ApoE is acceptable for any degree of icteric CSF samples.

TABLE 11

| | Icteric | | | |
|---|---|---|---|---|
| | Baseline | Lite | Moderate | Gross |
| 2/2 | | | | |
| Expected | 2/2 | 2/2 | 2/2 | 2/2 |
| Run 1 | 2/2 | 2/2 | 2/2 | 2/2 |
| Run 2 | 2/2 | 2/2 | 2/2 | 2/2 |
| Run 3 | 2/2 | 2/2 | 2/2 | 2/2 |
| Accuracy | 100% | 100% | 100% | 100% |
| 2/3 | | | | |
| Expected | 2/3 | 2/3 | 2/3 | 2/3 |
| Run 1 | 2/3 | 2/3 | 2/3 | 2/3 |
| Run 2 | 2/3 | 2/3 | 2/3 | 2/3 |
| Run 3 | 2/3 | 2/3 | 2/3 | 2/3 |
| Accuracy | 100% | 100% | 100% | 100% |
| 2/4 | | | | |
| Expected | 2/4 | 2/4 | 2/4 | 2/4 |
| Run 1 | 2/4 | 2/4 | 2/4 | 2/4 |
| Run 2 | 2/4 | 2/4 | 2/4 | 2/4 |
| Run 3 | 2/4 | 2/4 | 2/4 | 2/4 |
| Accuracy | 100% | 100% | 100% | 100% |
| 3/3 | | | | |
| Expected | 3/3 | 3/3 | 3/3 | 3/3 |
| Run 1 | 3/3 | 3/3 | 3/3 | 3/3 |
| Run 2 | 3/3 | 3/3 | 3/3 | 3/3 |
| Run 3 | 3/3 | 3/3 | 3/3 | 3/3 |
| Accuracy | 100% | 100% | 100% | 100% |
| 3/4 | | | | |
| Expected | 3/4 | 3/4 | 3/4 | 3/4 |
| Run 1 | 3/4 | 3/4 | 3/4 | 3/4 |
| Run 2 | 3/4 | 3/4 | 3/4 | 3/4 |
| Run 3 | 3/4 | 3/4 | 3/4 | 3/4 |
| Accuracy | 100% | 100% | 100% | 100% |
| 4/4 | | | | |
| Expected | 4/4 | 4/4 | 4/4 | 4/4 |
| Run 1 | 4/4 | 4/4 | 4/4 | 4/4 |
| Run 2 | 4/4 | 4/4 | 4/4 | 4/4 |
| Run 3 | 4/4 | 4/4 | 4/4 | 4/4 |
| Accuracy | 100% | 100% | 100% | 100% |

Ion Suppression: Ten patient samples were extracted. The ten samples were injected through the analytical column while the digested peptide mix of ApoE was infused post-column. If the total ion chromatogram (TIC) for ApoE showed a decrease of ≥15% of signal intensity when the internal standard for ApoE eluted, then ion suppression would be determined to be present in the assay. The TIC of the digested peptides ApoE showed no suppression in the gradient when the analyte is eluting. The TIC signal intensity is a flat line and shows ≤15% difference in signal intensity which is within the acceptable parameters of the assay.

Quantitative analysis of Total ApoE: The CSF Apolipoprotein E (ApoE) by LC-MS/MS assay measures total levels of ApoE in CSF. In order to measure total ApoE, a tryptic protein digestion is performed and a unique peptide to all three isoforms (ApoE2, ApoE3, and ApoE4) is used as surrogate to measure the total ApoE protein concentration. CSF ApoE samples are analyzed using tandem mass spectrometry with a Thermo Aria Cohesive TLX-4 high flow LC coupled with a Thermo Fisher Quantiva Triple Quadrupole mass spectrometer. The data is monitored in multiple reaction monitoring (MRM) and analyzed using Thermo Fisher LC Quant data analysis software. The following ions were measured:

| Compound | Precursor (m/z) | Product (m/z) | Collision Energy (V) | RF Lens (V) |
|---|---|---|---|---|
| Total ApoE: LGPLVEQGR | 485.06 | 489.51 | 18 | 55 |
| Total ApoE: LGPLVEQGR | 485.06 | 588.64 | 18 | 55 |
| Total ApoE IS: LQAEAFQAR(13C, 15N) | 522.54 | 602.6 | 18 | 55 |
| Total ApoE IS: LQAEAFQAR(13C, 15N) | 522.54 | 731.71 | 18 | 55 |

Limit of detection (LOD) for CSF ApoE: 0.33 ug/mL. The limit of quantitation for CSF ApoE is determined to be 1.0 ug/mL. LOB for CSF ApoE: 0.3 ug/mL.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the apolipoprotein E (ApoE) phenotype in a sample comprising cerebrospinal fluid, plasma, or serum, said method comprising:
   (a) digesting ApoE prior to purification, wherein the digesting comprises trypsin or microwave digestion;
   (b) purifying ApoE in the sample;
   (c) ionizing ApoE in the sample to produce one or more ion(s) of ApoE;
   (d) detecting the ion(s) from step (c) by mass spectrometry; and
   (e) determining the phenotype of ApoE allele(s) present in the sample from the ions detected in step (d), wherein the phenotype determined is ApoE2/ApoE2, ApoE2/ApoE4, ApoE3/ApoE3, ApoE3/ApoE4, or ApoE4/ApoE4; and
   wherein:
      the ApoE2/ApoE2 phenotype is determined by the presence of a fragment ion(s) having a mass/charge ratio selected from the group consisting of 665.72±0.5, 835.93±0.5, 866.99±0.5 and 982.08±0.5;
      the ApoE2/ApoE4 phenotype is determined by the presence of a fragment ion(s) having a mass/charge ratio selected from the group consisting of 374.42±0.5, 502.55±0.5, 649.74±0.5, 665.72±0.5, 835.93±0.5, 866.99±0.5, 892.96±0.5, and 982.08±0.5;
      the ApoE3/ApoE3 phenotype is determined by the presence of a fragment ion(s) having a mass/charge ratio selected from the group consisting of 374.42±0.5, 502.55±0.5, 866.99±0.5 and 982.08±0.5;
      the ApoE3/ApoE4 phenotype is determined by the presence of a fragment ion(s) having a mass/charge ratio selected from the group consisting of 374.42±0.5, 502.55±0.5, 649.74±0.5, 866.99±0.5, 892.96±0.5, and 982.08±0.5; and
      the ApoE4/ApoE4 phenotype is determined by the presence of a fragment ion(s) having a mass/charge ratio selected from the group consisting of 374.42±0.5, 502.55±0.5, 649.74±0.5, and 892.96±0.5.

2. The method of claim 1, wherein said purifying comprises liquid chromatography.

3. The method of claim 2, wherein said liquid chromatography comprises high performance liquid chromatography.

4. The method of claim 1, wherein said purifying comprises solid phase extraction.

5. The method of claim 1, wherein said ionization comprises electrospray ionization.

6. The method of claim 1, wherein said ionization comprises ionizing in positive mode.

7. The method of claim 1, further comprising adding an internal standard.

8. The method of claim 7, wherein said internal standard is isotopically labeled.

9. The method of claim 1, wherein the sample is cerebrospinal fluid.

10. The method of claim 1, wherein the sample is plasma or serum.

11. The method of claim 1, wherein the digestion comprises trypsin digestion.

12. The method of claim 1, wherein the digestion comprises microwave digestion.

13. The method of claim 1, wherein the presence of one or two ApoE4 alleles indicates increased risk of developing Alzheimer's disease.

* * * * *